US010913200B2

(12) United States Patent
Maggiore

(10) Patent No.: US 10,913,200 B2
(45) Date of Patent: Feb. 9, 2021

(54) DISPENSING DEVICE AND SYSTEM FOR BIOLOGICAL PRODUCTS

(71) Applicant: Sartorius Stedim Biotech GmbH, Goettingen (DE)

(72) Inventor: Frank Maggiore, Port Jefferson Station, NY (US)

(73) Assignee: Sartorius Stedim Biotech GmbH

( * ) Notice: Subject to any disclaimer, the term of this patent is extended or adjusted under 35 U.S.C. 154(b) by 4 days.

(21) Appl. No.: 15/409,669

(22) Filed: Jan. 19, 2017

(65) Prior Publication Data

US 2017/0335271 A1    Nov. 23, 2017

Related U.S. Application Data

(62) Division of application No. 15/159,858, filed on May 20, 2016.

(51) Int. Cl.
| | |
|---|---|
| *B29C 64/106* | (2017.01) |
| *B33Y 30/00* | (2015.01) |
| *B29C 64/20* | (2017.01) |
| *B33Y 10/00* | (2015.01) |
| *B29C 48/02* | (2019.01) |
| *B29C 48/00* | (2019.01) |
| *B65D 83/20* | (2006.01) |

(Continued)

(52) U.S. Cl.
CPC ............ *B29C 64/106* (2017.08); *B29C 48/02* (2019.02); *B29C 48/022* (2019.02); *B29C 64/20* (2017.08); *B33Y 10/00* (2014.12); *B33Y 30/00* (2014.12); *B01L 3/0293* (2013.01); *B01L 2200/0684* (2013.01); *B01L 2300/185* (2013.01); *B01L 2300/1877* (2013.01); *B01L 2300/1883* (2013.01); *B01L 2400/0487* (2013.01); *B25J 13/006* (2013.01); *B65D 81/3288* (2013.01); *B65D 83/202* (2013.01); *B65D 83/206* (2013.01); *B65D 83/68* (2013.01); *C12M 23/28* (2013.01); *C12M 33/00* (2013.01); *C12M 37/00* (2013.01); *C12M 41/48* (2013.01)

(58) Field of Classification Search
None
See application file for complete search history.

(56) References Cited

U.S. PATENT DOCUMENTS

| | | | | |
|---|---|---|---|---|
| 3,084,871 A | * | 4/1963 | Puglis ................. | B65D 83/386 239/305 |
| 3,604,597 A | * | 9/1971 | Pohl .................... | B29C 66/8167 222/146.5 |

(Continued)

*Primary Examiner* — Joseph S Del Sole
*Assistant Examiner* — Manley L Cummins, IV
(74) *Attorney, Agent, or Firm* — Gerald E. Hespos; Michael J. Porco; Matthew T. Hespos

(57) ABSTRACT

A dispensing system has a sterilizable chamber. At least one robotic arm assembly and a dispensing device are within the sterilizable chamber. The dispensing device comprising a first dispensing element and a second dispensing element. The first dispensing element is connectable to the second dispensing element The at least one robotic assembly is configured to move the dispensing device. An external control device is connected to the at least one robotic arm assembly and is configured to control the at least one robotic arm assembly. The first dispensing element is configured to dispense a structural material and the second dispensing element is configured to dispense a biological material.

11 Claims, 11 Drawing Sheets

(51) Int. Cl.
*B65D 83/68* (2006.01)
*B65D 81/32* (2006.01)
*B01L 3/02* (2006.01)
*C12M 1/00* (2006.01)
*C12M 1/26* (2006.01)
*C12M 1/36* (2006.01)
*B25J 13/00* (2006.01)
*C12M 1/12* (2006.01)

(56) References Cited

U.S. PATENT DOCUMENTS

| | | | | |
|---|---|---|---|---|
| 3,665,158 | A * | 5/1972 | Froedge | B05C 17/00523 219/421 |
| 5,021,217 | A * | 6/1991 | Oshikubo | B01L 3/0217 422/516 |
| 5,121,329 | A * | 6/1992 | Crump | G05B 19/4099 700/119 |
| 5,150,819 | A | 9/1992 | Johnson | |
| 6,041,977 | A * | 3/2000 | Lisi | A21C 15/005 222/179 |
| 6,149,622 | A * | 11/2000 | Marie | A61M 1/0043 604/119 |
| 6,150,581 | A * | 11/2000 | Jiang | A61K 31/734 602/50 |
| 6,152,333 | A * | 11/2000 | Binder | B05C 17/015 222/333 |
| 6,460,481 | B1 * | 10/2002 | Young | A23G 3/28 118/14 |
| 7,500,846 | B2 * | 3/2009 | Eshed | B33Y 30/00 425/375 |
| 7,625,198 | B2 * | 12/2009 | Lipson | A61L 27/36 425/174 |
| 7,950,549 | B1 * | 5/2011 | Harris | A23G 3/28 222/333 |
| 8,834,793 | B2 | 9/2014 | Koltay | |
| 9,102,098 | B2 | 8/2015 | Dilworth | |
| 9,327,397 | B1 * | 5/2016 | Williams | B25J 3/00 |
| 2003/0065400 | A1 * | 4/2003 | Beam | A61L 27/12 623/23.51 |
| 2003/0100824 | A1 * | 5/2003 | Warren | A61B 5/0066 600/407 |
| 2003/0138556 | A1 | 7/2003 | Binder | |
| 2004/0059283 | A1 * | 3/2004 | Kirwan | B05C 17/015 604/23 |
| 2004/0237822 | A1 * | 12/2004 | Boland | B01L 3/0268 101/483 |
| 2005/0072412 | A1 * | 4/2005 | Cuisinier | F41B 9/0078 124/1 |
| 2006/0054039 | A1 | 3/2006 | Kritchman | |
| 2009/0050706 | A1 | 2/2009 | Xu | |
| 2010/0283172 | A1 | 11/2010 | Swanson | |
| 2014/0061974 | A1 * | 3/2014 | Tyler | B29C 64/393 264/401 |
| 2014/0154347 | A1 * | 6/2014 | Dilworth | B33Y 30/00 425/87 |
| 2014/0271964 | A1 | 9/2014 | Roberts, IV | |
| 2015/0035206 | A1 * | 2/2015 | Maggiore | B29C 67/0085 264/401 |
| 2015/0105891 | A1 * | 4/2015 | Golway | G06B 30/20 700/98 |
| 2015/0142159 | A1 * | 5/2015 | Chang | B29C 67/0007 700/119 |
| 2015/0314613 | A1 * | 11/2015 | Murphy | G05B 19/27 435/283.1 |
| 2016/0038655 | A1 * | 2/2016 | Weisman | B33Y 30/00 264/0.5 |
| 2016/0059481 | A1 * | 3/2016 | Starodubtsev | B29C 64/112 264/494 |
| 2016/0075089 | A1 * | 3/2016 | Duro Royo | B29C 64/386 264/308 |
| 2016/0108261 | A1 * | 4/2016 | Wiseman | C09D 11/16 401/143 |
| 2016/0136895 | A1 * | 5/2016 | Beyer | B29C 64/209 264/241 |
| 2016/0185028 | A1 * | 6/2016 | Bogue | B29C 48/02 425/162 |
| 2016/0229121 | A1 * | 8/2016 | Ilic | B29C 64/20 |
| 2016/0236408 | A1 * | 8/2016 | Wolf | B33Y 30/00 |
| 2016/0288414 | A1 * | 10/2016 | Ozbolat | B29C 64/106 |
| 2017/0001301 | A1 * | 1/2017 | Kamiya | B25J 9/1689 |
| 2017/0095976 | A1 * | 4/2017 | Pedersen | B29C 64/209 |
| 2017/0172765 | A1 * | 6/2017 | Solorzano | B29C 64/264 |
| 2017/0190118 | A1 * | 7/2017 | Mire | B29C 48/02 |
| 2017/0217088 | A1 * | 8/2017 | Boyd, IV | B29C 64/106 |
| 2018/0009161 | A1 * | 1/2018 | Cowen | B33Y 30/00 |

* cited by examiner

DISPENSING DEVICE AND SYSTEM FOR BIOLOGICAL PRODUCTS

BACKGROUND

1. Field of the Invention

The application relates to a handheld dispensing device, as well as a system provided therewith, and a dispensing system comprising a sterilizable chamber.

2. Description of the Related Art

Three-dimensional (3D) bioprinting is the process of employing 3D printing technologies using materials such as cells and supporting components in order to create e.g. cell patterns and living tissues, wherein the cell function and viability are preserved within the printed construct. Recently, 3D bioprinting has begun to incorporate the printing of scaffolds, i.e. structures providing support for the cells.

Current state-of-the-art solutions for 3D bioprinting are large 3D printing machines with components that move over a printing tray filled e.g. with nutrient rich media, potentially causing particle shedding into the tray. An example of a single-use biological 3D printer is given in US 2015/0035206 A1.

Alternatively, small-scale solutions such as pen printers are available. For example, U.S. Pat. No. 8,834,793 B2 discloses a pen capable of dispensing biological material, whereas U.S. Pat. No. 9,102,098 B2 discloses a pen capable of dispensing structural material used for printing scaffolds. Generally, structural material (e.g. thermoplastic) pen printers and biological material pen printers (such as cell dispensers) exist separately. The ARC Centre of Excellence for Electromaterials Science developed a pen that extrudes cell material inside a biopolymer such as alginate, which is in turn encased in an outer layer of gel material. Both the outer and inner layers are combined in the pen head as it is extruded. However, the pen must be sterilized after every use and it may be cumbersome to comply with the required sterilization conditions.

There is therefore a need for a system allowing a biological material to be added to structural material and scaffolding to efficiently and easily form a plurality of objects under sterile conditions. In particular, a handheld device allowing a user to quickly, easily, and cheaply try out multiple designs at the small-scale while checking for structural material and cell compatibility and optimizing their process prior to e.g. scaling up to a large-scale biological 3D printer is needed.

One application may be for laboratories and biopharma companies to quickly screen materials, scaffolding designs, and shapes to test their cells and bioactive materials for material compatibility and to optimize their process prior to scale-up. The primary application for the biopharma industry may be for screening of 3D printed cell products for efficacy and toxicity testing prior to use with the single-use biological 3D printers. This small-scale lab technology may additionally be applied to the screening the customer's bioactive materials for In Vitro Diagnostic (IVD) tests on diagnostic membranes such as the UniSart line of products, printing on biosensors, as well as a variety of custom medical devices.

SUMMARY

According to one aspect, a handheld dispensing device is provided. The handheld dispensing device comprises the following: a first dispensing element configured to dispense a structural material; and a second dispensing element configured to dispense a biological material; wherein the second dispensing element is single-use and sterilizable; and wherein the first dispensing element is releasably connectable to the second dispensing element.

According to another aspect, a system is provided. The system comprises the following: a handheld dispensing device according to the first aspect; at least one single-use bioreactor; and at least one aseptic connection assembly configured to connect the at least one single-use bioreactor to the handheld dispensing device.

According to a further aspect, a dispensing system is provided. The dispensing system comprises the following: a sterilizable chamber; at least one robotic arm assembly and a dispensing device within the sterilizable chamber, wherein the at least one robotic assembly is configured to move the dispensing device comprising a first dispensing element and a second dispensing element, the first dispensing element being releasably connectable to the second dispensing element; and an external control device connected to the at least one robotic arm assembly and configured to control the at least one robotic arm assembly; wherein the first dispensing element is configured to dispense a structural material and the second dispensing element is configured to dispense a biological material.

Details of exemplary embodiments are set forth below with reference to the exemplary drawings. Other features will be apparent from the description, the drawings, and from the claims.

DETAILED DESCRIPTION

Figure 1:
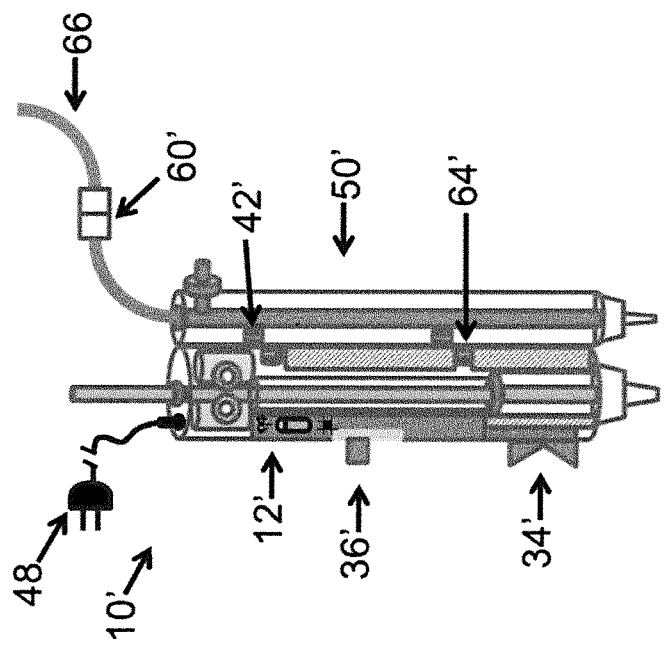
FIGS. 1A and 1B shows an example of a handheld dispensing device comprising an attachment mechanism.
Figure 1:
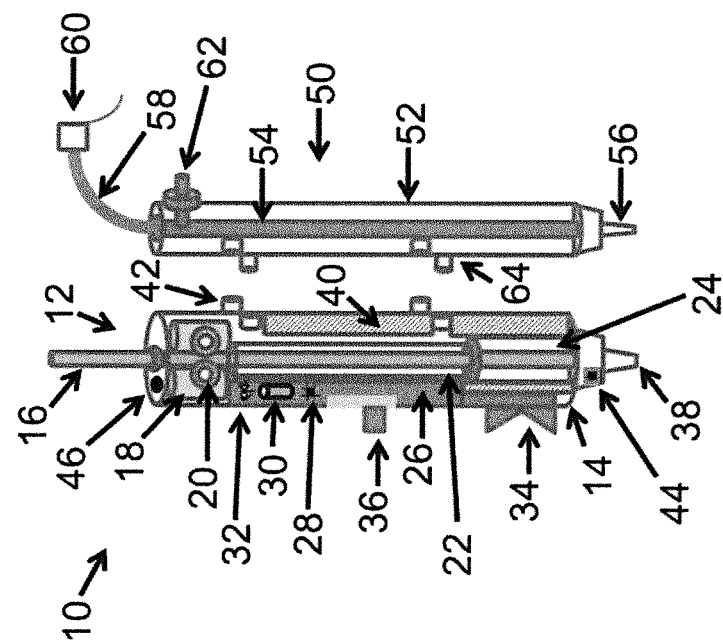

In the following text, a detailed description of examples will be given with reference to the drawings. It should be understood that various modifications to the examples may be made. In particular, one or more elements of one example may be combined and used in other examples to form new examples. In the following, reference numbers with a prime denote the same components as the corresponding plain numbers but in a different configuration. For example, 10 denotes a dispensing device in a disconnected state and 10' denotes a dispensing device in a connected state.

FIGS. 1A to 11 show different examples of a dispensing device that can supply both a structural material and a biological material for additive manufacturing. In other words, the materials being extruded by the dispensing device can be used to print, i.e. create, 3D objects. A 3D object is any object that exists in the three dimensions of space, regardless of the measures of its length, width and depth and the ratios thereof.

Structural materials encompass materials whose primary purpose is to carry the loads and/or maintain the juxtaposition of the component parts of a system. Structural materials are load or stress bearing, wherein the stress can be induced either mechanically, thermally or a combination of both. Structural materials may be used to build scaffolds, i.e. structures providing support for cells and other materials derived from a biological system. The architecture of the scaffold is important for e.g. structural, nutrient transport, and cell-matrix interaction conditions. Examples of structural materials are heated thermoplastics, hydrogels, cellulose, collagen, collagen fibers, bio-paper (and other dissolvable materials), sugars, epoxies, synthetic polymers.

Biological materials may include materials comprising a biological system, such as cells, cell components, cell products, and other molecules, as well as materials derived from a biological system, such as proteins, antibodies and growth factors. The dispensing device may in addition dispense other materials related to the biological material, e.g. supportive fluids such as nutrient rich media and metered drug products.

The dispensing device described here provides a platform for dispensing structural materials to form a scaffold or a three dimensional printed object as well as biological materials that may be dispensed onto the structural materials to form a printed product. A wide variety of structures such as cell structures, biological products, implants, scaffolding structures, diagnostic kits, etc. may be printed.

The dispensing device can utilize a variety of different techniques of additive manufacturing whereby materials are built up layer-by-layer to form the 3D products. The dispensing means may include but are not limited to an extrusion printing head that deposits a solid, fluid, or semi-solid material in a continuous stream or in droplets, a heated extrusion printing head that can heat a solid material to help it flow as a fluid where it can solidify once printed onto a platform, and a spray deposition printing head which sprays micronized droplets of a material over a specific area within a pattern.

Figure 8:
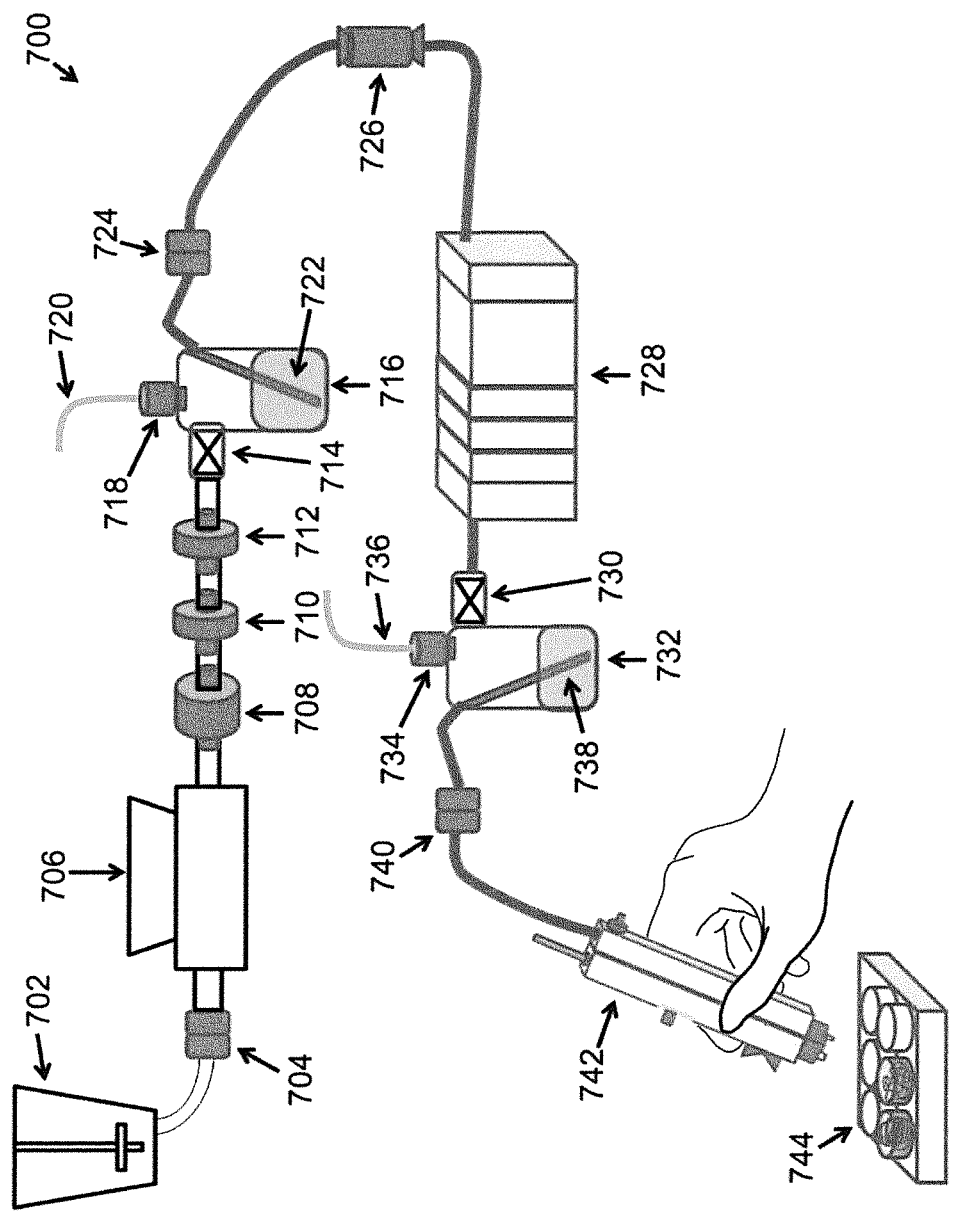
FIG. 8 shows an example of a system comprising a handheld dispensing device, a biological material source, a centrifugation assembly and a crossflow assembly.
Figure 9:
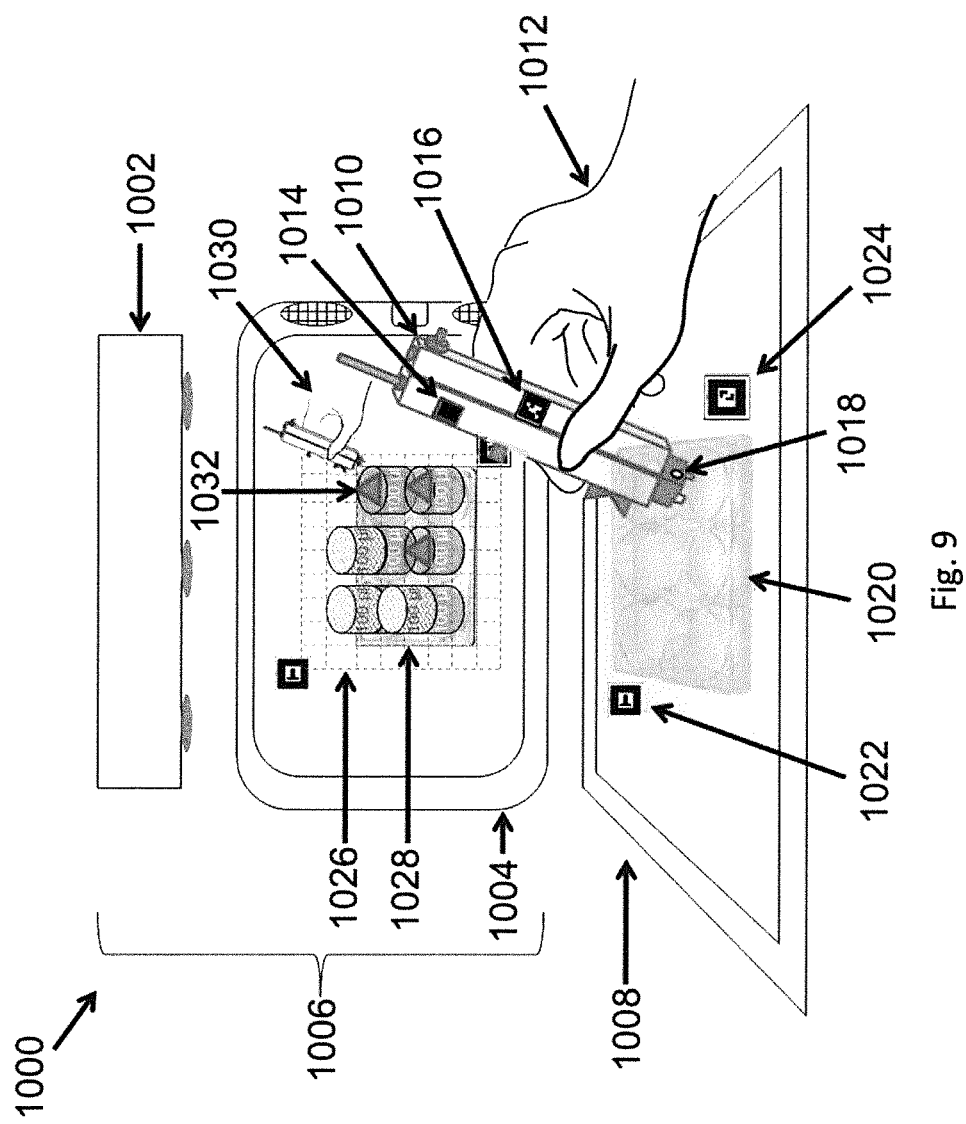
FIG. 9 shows an example of an external monitoring setup for the monitoring of a handheld dispensing device.
Figure 10:
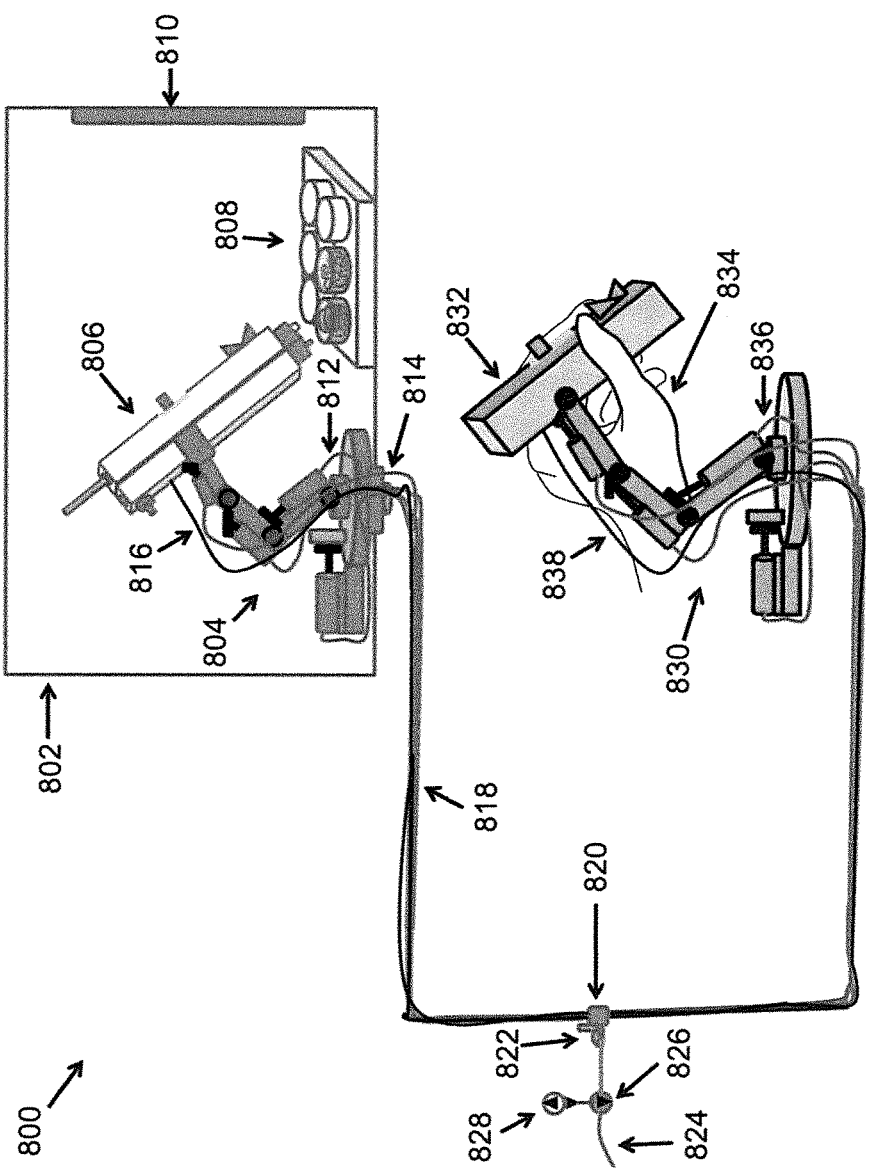
FIG. 10 shows an example of a dispensing system comprising a sterilizable chamber, a dispensing device and a manually-operated external control device.
Figure 11:
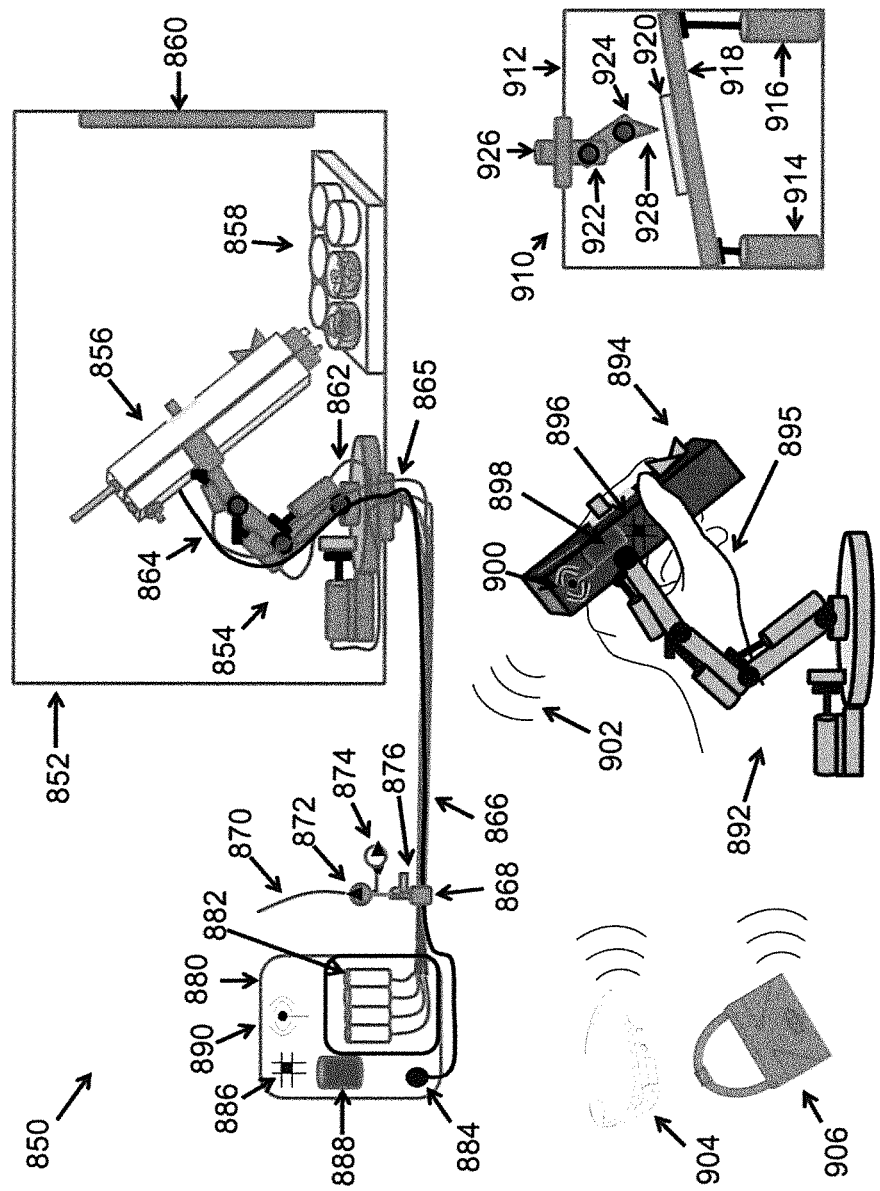
FIG. 11 shows an example of a dispensing system comprising a sterilizable chamber, a dispensing device and a automatically-operated external control device.

The dispensing device may be a handheld device held directly by an operator, as shown in FIGS. 1A to 9, or it may be controlled by a robotic control tool, as shown in FIGS. 10 and 11. According to one example, the robotic control tool may be manually controlled by an operator via a communication with a stylus simulant maneuvered by the operator. According to another example, the robotic control tool may run a pre-programmed operation for printing.

The dispensing device may comprise at least two dispensing elements, the first dispensing element configured to dispense the structural material and the second dispensing element configured to dispense the biological material. In some examples, the dispensing device may comprise additional dispensing elements, e.g. for dispensing material related to the biological material, for example material required to preserve the biological material and/or its viability, such as supportive fluids. The additional dispensing elements may include, but are not limited to, a pipette dispensing element, a fluid dispensing element, a spray coating dispensing element, a metered drug dispenser, a nutrient rich media dispenser, a gel dispenser, a sputter coating dispenser, and an adhesive dispensing tool. One or more of the dispensing elements may comprise hydraulic, pneumatic, magnetic, electric, and/or manual drive mechanisms configured to control the movement of the material until it is dispensed from a dispensing tip. In one example, the drive mechanism may comprise at least one feed motor.

Additionally or alternatively, the dispensing device may comprise one or more modification tools for modifying the printed object. The modification tools may include but are not limited to a puncturing tool, a blade, a cutting tool, a rotating screw, a grinding tool, an imprinting tool, a stamping tool, and a laser cutter tool.

Exemplarily, the dispensing device may comprise a material selector switch to select which dispensing element among the plurality of dispensing elements in the dispensing device should dispense its material. In other words, the material selector switch may select the material to be dispensed by the dispensing device.

The first dispensing element (also referred to as "structural material dispensing element") and the second dispensing element (also referred to as "biological material dispensing element") may be fixedly or releasably connectable to each other. Similarly, the additional dispensing elements and/or modification tools may be connectable. The dispensing elements may be directly connected, e.g. physically contacting each other, or indirectly connected, e.g. via a third element. The connection between the dispensing elements may allow power, data (e.g. sensor data, input data) and/or fluid communication between the dispensing elements.

In some examples, the dispensing elements are permanently connected to each other, in that the dispensing device is formed as a whole. In other examples the dispensing elements may be releasably connectable. In other words, the dispensing elements may exist in a physically separated state or in a connected state, and it is possible to switch back and forth from one state to the other. The releasable connection may be accomplished via an attachment mechanism, such as a snap mechanism including protrusions and corresponding fitted holes to accommodate the protrusions. Other attachment mechanisms may comprise but are not limited to displaceable locking tabs and fitted receiving holders, fasteners and magnets.

In some examples, the dispensing device may comprise barriers between the dispensing elements to prevent undesired effects due to the proximity of the dispensing elements when connected. Exemplarily, the first dispensing element may comprise a heating element to heat the structural material and a barrier (e.g. a thermal barrier) may shield the biological material, preventing the heating from negatively affecting the biological material in the second dispensing element.

At least the second dispensing element is a sterilizable, single-use element to prevent cross contamination from one batch of biological material to another. A single-use element is a disposable element, i.e. an element that is discarded after being used. The single-use element is configured for a one-time use and, after it has been used once, it has fulfilled its function and may be disposed of. A single-use element is formed from sterilizable materials and helps reduce the risk of contaminations because of its disposability.

The sterilizable, single-use biological material dispensing element may be delivered pre-sterilized, such as by gamma-irradiation, or be sterilized by the operator using a validated sterilization method, such as by autoclaving, prior to use. The sterilizable, single-use biological material dispensing element may connect with the current infrastructure of bioreactors, both multi-use and single-use, micro-bioreactors, filters, and other bioprocessing devices through standardized aseptic connectors. For example, the biological material dispensing element may utilize an aseptic connection to a biological material feed source such as a bioreactor vessel. The biological material from the feed source may undergo processing such as filtration, concentration, etc., prior to dispensing from the dispensing element.

According to one example, the sterilizable, single-use biological material dispensing element may be connected to a multi-use structural material dispensing element. According to another example, the entire dispensing device comprising the first and second dispensing elements may be sterilizable and single-use.

The dispensing device is intended to allow an operator to quickly screen for structural material compatibility with biological materials. The operator is able to easily create a plurality of shapes, designs, structures, scaffolding, and printing procedures to optimize for the best combination. Essentially this is determining if the material types and shapes printed are compatible for maintaining or promoting cell growth and optimizing the conditions for such growth prior to scaling up activities to a large-scale biological 3D printer, such as a single-use printer assembly.

The dispensing device may contain one or more orientation and positioning sensors or may be positionally tracked by an external monitoring device to record the movements, materials dispensed, and conditions. This stored positional file of the recorded movements of the dispensing device may be utilized to replicate a qualified printed design from the small-scale dispensing device within a large-scale biological 3D printer. In other words, the stored information regarding the method and conditions of dispensing may be used to print with a 3D printer the structural materials and biological materials in the exact same way an operator constructed a three dimensional object using the dispensing device.

FIGS. 1A and 1B shows an example of a handheld dispensing device 10 comprising an attachment mechanism. A sterilizable, single-use biological material dispensing element 50 is directly connected to a multi-use structural material dispensing element 12 using the attachment mechanism. FIG. 1A is a side view of the dispensing device 10 in a disconnected state, wherein the dispensing device 10 comprises the first dispensing element 12 and the second dispensing element 50 disconnected from each other.

The structural material dispensing element 12 of the dispensing device 10 may comprise a printer body 14 that encloses a plurality of components. The multi-use structural material dispensing element 12 of the dispensing device 10 may utilize a structural material 16, which for example is a thermoplastic material, such as polylactic acid (PLA), acrylonitrile butadiene styrene (ABS), carbon fiber, low melting point metals and/or other low melting point structural materials. In other examples, the structural material may consist of but is not limited to hydroxyapatite (HA), collagen, fibrin, hydrogels, chitosan, hyaluronic acid, sugars, gels, powders.

In this example, a length of thermoplastic structural material 16 may be inserted into the top of the multi-use structural material dispensing element 12 and the dispensing speed is determined by a feed motor 18 that has at least one gear 20 to control the movement of the thermoplastic structural material 16. A plurality of feed motors 18 and gears 20 may be utilized to ensure a steady flow of the structural material 16 through the top of the dispensing element 12 until it is dispensed from a dispensing tip 38 to prevent jamming internally within the device.

The structural material 16 may move through an internal tube 22 to a heating element 24 such as an electrically-powered heating element, which is powered through an electrical connection 46. In this example, the heating of the thermoplastic structural material 16 and the dispensing through the narrow dispensing tip 38 may constitute a form of ultra-pasteurization that can kill off micro-organisms within the structural material 16 even if it is from a non-sterile feedstock. Other dispensing methods without heating or compression may require aseptic connection to a sterile feedstock prior to use.

An operator may control the temperature of the heating element 24 and the dispensing of the structural material 16 through a computer control board 26 that may contain a processing device 28, a memory storage device 30, and a wireless communications device 32. The multi-use structural material dispensing element 12 may comprise one or a plurality of controlling devices to allow the operator to control the flow of material, e.g. utilizing dispense and retraction buttons 34. Furthermore, a material selector switch 36 may be provided to select which material from a plurality of materials should be dispensed by the dispensing device 10, such as switching from the dispensing of a structural material 16 to the dispensing of a biological material, once the second dispensing element 50 is connected to the first dispensing element 12. Additionally or alternatively a remote input device (not shown) may be utilized, such as a wired or wireless foot pedal, a wearable device, or other remote input, to control the flow of material and the selection of materials to dispense.

The dispensing device 10 may contain in the first dispensing element 12 a plurality of positional sensors 44 including but not limited to motion sensors, orientation sensors, gyroscopic sensors, environmental sensors, cameras, microscopic cameras, thermal cameras, depth sensors, ultrasound devices, magnetometers, accelerometers, proximity sensors, global positioning system (GPS) devices, internal measurement units (IMUs) and internal or external positioning sensors. The information from the orientation and positioning of the dispensing device 10 used by an operator can be saved into a file, which may be utilized to print out a replica of the structural materials and biological materials in the exact same way as was manually printed utilizing a large-scale single-use biological 3D printer setup (not shown). Additionally or alternatively the sensors utilized for positioning may also be utilized to scan the workspace, the printing tray, and/or the three dimensional object prior to, during, and/or after printing. These scans may be utilized to determine the structure or microstructures of the printed materials.

The multi-use structural material dispensing element 12 of the dispensing device 10 may use an attachment mechanism 42, e.g. a snap mechanism, to attach to a corresponding attachment mechanism 64 on the single-use biological material dispensing element 50. In this example, the dispensing elements 12 and 50 are directly connected. The attachment mechanism 42 may bring the single-use biological material dispensing element 50 in communicative connection with the multi-use structural material dispensing element 12, wherein the connection may establish an electrical, mechanical, and/or fluid communication. In this example the connection between the multi-use structural material dispensing element 12 and the single-use biological material dispensing element 50 may contain a thermal barrier 40 to prevent excess heat from the heating element 24 to negatively impact the dispensing of the biological materials.

The single-use biological material dispensing element 50 may be constructed of sterilizable materials and may be sterilized utilizing a validated method, such as gamma irradiation, autoclaving, and/or chemical sterilization. For example, the single-use biological material dispensing element 50 may consist of a printer body 52 that encloses a plurality of components. Furthermore, it may include at least one physical aseptic connector that may comprise two or more components, such as an OPTA® connector with a tubing to connect to an external sterile feed source of cells, media, and/or other biological materials, as well as a tubing component 58 that transports the sterile feed material from the aseptic connection to an internal tubing 54. Alternatively the aseptic connection may be made with at least one thermoweldable tubing which can be connected using a Biowelder® thermoweldable tubing sealer (not shown).

The internal tubing 54 runs the length of the printer body 52 until a dispensing tip 56 situated at the end opposite the tubing component 58. The dispensing tip 56 may comprise a plurality of shapes to alter the dispensing profile of the dispensed material, such as slow and focused or sprayed over a defined area or pattern. The dispensing tip 56 may additionally contain a restriction device (not shown) that may partially close to restrict the material flow through the tip 56 or completely close to stop the flow of all material through the tip 56. Alternatively the operator may select between a plurality of dispensing tips, with different geometries for different dispensing patterns, which may be selected by moving a carousel wheel containing multiple tip configurations (not shown) on the printer body 52 or by attaching pre-sterilized tips (not shown) to the dispensing tip 56.

A vent filter 62, such as an integrity-testable, sterilizing-grade vent filter, may be utilized to properly vent the internal tubing 54 as it fills with material. The movement of the material through the single-use biological material dispensing element 50 may be provided by an external source such as a pneumatic pressure source, a pump, or an electric motor. Alternatively, the pump, electric motor, and/or pneumatic pressure source may be internal to the dispensing device 10.

FIG. 1B is a side view of the dispensing device 10' in a connected state. In this example the multi-use structural material dispensing element 12' is connected using attachment mechanism 42', which is attached to the corresponding attachment mechanism 64' on the single-use biological material dispensing element 50'. The material selector switch 36' may be moved from a position for selecting the multi-use structural material dispensing element 12' to a position for selecting the single-use biological material dispensing element 50', so the biological material and/or material related to the biological material may be dispensed by the operator utilizing the material dispensing and retraction buttons. The dispensing device 10' in the connected state may contain an ergonomically-molded handgrip on either the material dispensing element 12', the single-use biological material dispensing element 50', or across both elements for the comfort of the operator using the device.

A power cable 48 may be plugged into the electrical connection 46 to power the electric heating element 24, the at least one feed motor 18, or other electronic components. Alternatively, the dispensing device 10 may be powered by at least one of a battery that is exemplarily rechargeable, an alternate wired connection, a powered communication port, a solar cell, a mechanical power source, an electromechanical power source such as a hand crank, or a wireless power source.

The single-use biological material dispensing element 50' may be connected to a biological feed source 66 via the at least one aseptic connection 60'. The aseptic connection 60' may be made using an aseptic connector such as an OPTA® connector and/or other physical aseptic connector, and/or may be achieved by thermowelding a tubing length of thermoweldable tubing to the feed assembly for a sterile connection with the biological feed source 66.

FIGS. 2A-2D shows an example of a handheld dispensing device 100 comprising a body provided with at least one sleeve 120.

FIG. 2A is a side view of the handheld dispensing device 100 in a disconnected state. The dispensing device 100 comprises a reusable multi-use structural material dispensing element 102 and the sleeve 120 for inserting a sterilizable, single-use biological material dispensing element 122. The multi-use structural material dispensing element 102 of the dispensing device 100 may comprise a printer body 104 that encloses a plurality of components. In one example, the sleeve 120 may be a part of the printer body 104, so that the dispensing elements 120 and 122 are directly connected.

The multi-use structural material dispensing element 102 may utilize a structural material 106 such as a thermoplastic material. In other examples the structural material may comprise any of hydroxyapatite (HA), collagen, fibrin, hydrogels, chitosan, hyaluronic acid, sugars, gels, powders.

In this example a length of thermoplastic structural material 106 may be inserted into the top of the multi-use structural material dispensing element 102 and the dispensing speed may be determined by a feed motor which has one or more gears to control the movement of the thermoplastic structural material 106. The structural material 106 may move through an internal tube towards a heating element 108, which may heat the thermoplastic structural material 106 and dispense it through a narrow dispensing tip 112.

An operator may control the temperature of the heating element 108 and the dispensing of the structural material 106 through a computer control board 114 that may contain a processing device, a memory storage device, and a wireless communications device. The multi-use structural material dispensing element 102 may comprise one or a plurality of controlling devices to allow the operator to control the flow of material, e.g. utilizing dispense and retraction buttons 110 and a material selector switch 116, which selects a material from a plurality of dispensing materials. Exemplarily, once the single-use biological material dispensing element 122 is connected to the structural material dispensing element 102, the material selector switch may switch from the dispensing of the structural material 106 to the dispensing of a biological material.

The dispensing device 100 may contain a plurality of positional sensors 118 including but not limited to motion sensors, orientation sensors, gyroscopic sensors, environmental sensors, cameras, depth sensors, magnetometers, accelerometers, proximity sensors, GPS devices, and internal or external positioning sensors.

The printer body 104 of the multi-use structural material dispensing element 102 may contain a barrel or sleeve 120 into which the single-use biological material dispensing element 122 may be inserted. The connection between the dispensing elements 102 and 122 via insertion into the barrel 120 may be further aided by an attachment mechanism, such as a snap mechanism. In this example, the dispensing elements 102 and 122 are directly connected. The insertion of the single-use biological material dispensing element 122 and the optional attachment to the attachment mechanism may bring the dispensing element 122 in communicative contact with the multi-use structural material dispensing element 102. The connection may establish an electrical, mechanical, and/or fluid communication. In this example the connection between the multi-use structural material dispensing element 102 and the single-use biological material dispensing element 122 may contain a thermal barrier to prevent excess heat from the heating element 108 to negatively impact the dispensing of the biological materials.

The single-use biological material dispensing element 122 may be constructed of sterilizable materials and may be sterilized utilizing a validated method, such as gamma irradiation, autoclaving, and/or chemical sterilization. Exemplarily, the single-use biological material dispensing element 122 may comprise a printer body that encloses a plurality of components. Furthermore, the dispensing element 122 may include at least one physical aseptic connector 124 that may comprise two or more components, such as an OPTA® connector with a tubing component 126 to connect to an external sterile feed source of cells, media, and/or other biological materials, wherein the tubing component 126 may transport the sterile feed material from the aseptic connection to an internal tubing 128. Alternatively the aseptic connection may be made with at least one thermoweldable tubing that can be connected using a Biowelder® thermoweldable tubing sealer (not shown).

The internal tubing 128 may run the length of the printer body until a dispensing tip 132 at one end opposite the end connected to the tubing component 126. The dispensing tip 132 may comprise a plurality of shapes to alter the dispensing profile of the dispensed material, such as slow and focused or sprayed over a defined area or pattern. A vent filter 134, such as an integrity-testable, sterilizing-grade vent filter, may be utilized to properly vent the internal tubing 128 as it fills with material.

The movement of the material through the single-use biological material dispensing element 122 may be provided by an external source such as a pneumatic pressure source, a pump, or an electric motor. Alternatively, the pump, electric motor, and/or pneumatic pressure source may be internal to the dispensing device 100.

FIG. 2B is a side view of the dispensing device 100' in a connected state. In this example the single-use biological material dispensing element 122' may be inserted into the sleeve 120 and further connected using an attachment mechanism. The material selector switch 116' may be moved from a position for selecting the multi-use structural material dispensing element 102' to a position for selecting the single-use biological material dispensing element 122', so the biological material and/or material related to the biological material may be dispensed by the operator utilizing the material dispensing and retraction buttons 110. The dispensing device 100' in the connected state may contain an ergonomically-molded handgrip on the material dispensing element body 102' for the comfort of the operator using the device.

The single-use biological material dispensing element 122' may be connected to a biological feed source 130 via at least one aseptic connection 124'. The aseptic connection 124' may be achieved by thermowelding a tubing length of thermoweldable tubing to the feed assembly for a sterile connection with the biological feed source. The aseptic connection 124' may be made using an aseptic connector such as an OPTA® connector and/or other physical aseptic connector, and/or may be achieved by thermowelding a tubing length of thermoweldable tubing to the feed assembly for a sterile connection with the biological feed source.

The dispensing device 100' may be powered by a power cable (not shown), a battery, which is exemplarily rechargeable, a powered communication port, a solar cell, a mechanical power source, an electromechanical power source such as a hand crank, or a wireless power source.

FIG. 2C is a side view of a dispensing device 150 in a disconnected state. The structural material dispensing element 162 and the biological material dispensing element 164 may be similar to the corresponding elements described with reference to views 'A' and 'B'. However, the body of the structural material dispensing element 162 does not contain a sleeve. Rather, in this example, there is a central connection body 152 that contains a plurality of barrels or sleeves 154, 156 where the plurality of dispensing elements 162, 164 may be inserted to form a completed assembly. The dispensing elements 162 and 164 may thus be indirectly connected via the central connection body 152.

A further attachment mechanism may be used to fix the dispensing elements in the sleeves 154, 156. The attachment mechanism may bring the plurality of dispensing elements 162, 164 in communicative connection with the central connection body 152, wherein the connection may include electrical, mechanical, and/or fluid communication.

In this example the central connection body 152 may be sterilizable and single-use. The plurality of dispensing elements 162, 164 connecting to the central connection body 152 may additionally be sterilizable and single-use. The central connection body 152 may contain a thermal barrier 158 between the plurality of barrels 154, 156 to prevent thermal energy transfer from negatively affecting the biological material dispensing element 164. The central connection body 152 may additionally contain a plurality of controlling elements 160 such as buttons, switches, knobs, and other operator control elements similar to those described with reference to views 'A' and 'B'.

FIG. 2D is a side view of the dispensing device 150' where both the multi-use structural material dispensing element 162' and the single-use biological material dispensing element 164', separated by the thermal barrier 158, are in a connected state and attached to the central connection body 152 using an attachment mechanism. The central connection body 152 may contain an ergonomically-molded handgrip for the comfort of the operator using the device.

In this example the multi-use structural material dispensing element 162' may contain a computer control board comprising a processing device, a memory storage device, and a wireless communications device. The plurality of controlling elements 160 on the central connection body 152 may line up and communicatively attach to the computer control board elements to receive the inputs of the controlling elements 160. Alternatively the computer control board and other devices may be in part or in whole integrated into the central connection body 152.

The single-use biological material dispensing element 164' may be connected to a biological feed source, such as material originating from or processed from a multi-use or a single-use bioreactor, via at least one aseptic connection 166'. For example, the aseptic connection is made by an aseptic connector such as an OPTA® connector and/or other physical aseptic connector where two or more components 166', 168 are connected together. In other examples, the multi-use structural material dispensing element 102 may require an aseptic connection for some structural materials, such as hydrogels, hydroxyapatite (HA), collagen, fibrin, chitosan, hyaluronic acid, etc., which may be unable to be heated to extreme temperatures. Since the heating ensures the killing of all microorganisms in the structural material prior to dispensing, if heating is not possible, the feed material may require sterilization prior to connection to the dispensing device 150 to prevent any potential contamination of the final printed object.

As shown in FIGS. 1A-2D, the structural material dispensing element may generally comprise at least one feed motor to control the movement of the structural material, at least one internal tubing to contain the structural material and at least one dispensing tip from which the structural material is dispensed. Furthermore, the structural material dispensing element may comprise at least one controlling device (e.g. dispense and retraction buttons and/or material selector switch) to control the flow of the material and select which material must be dispensed when other dispensing elements are connected to the structural material dispensing element. Additionally or alternatively, the structural material dispensing element may comprise processing means, such as a computer control board, to control the dispensing process. Exemplarily, the structural material dispensing element may comprise a heating element to heat and melt the structural material, and the processing means may be configured to control the temperature of the heating element.

The biological material dispensing element may generally comprise a body formed out of sterilizable materials, at least one internal tubing to contain the biological material, at least one vent filter to properly vent the internal tubing as it fills with material, and at least one dispensing tip from which the biological material is dispensed. Additionally, the biological material dispensing element may comprise an aseptic connector to a material feed source for the sterile transfer and dispensing of the biological material.

The combination of the biological material dispensing element and the structural material dispensing element as described in FIGS. 1A-2D show only one of many possible configurations of a handheld dispensing device. FIGS. 3A-3D show other examples of a handheld dispensing device comprising an attachment mechanism, wherein a plurality of dispensing elements may be connected and/or an external barrier between connected dispensing elements may be provided.

FIG. 3A is a side view of a dispensing device 230 where a plurality of connectable dispensing elements are in the disconnected state. In this example the dispensing elements making up the dispensing device 230 may comprise a multi-use structural material dispensing element 232, a single-use biological material dispensing element 262, and a pipette liquid dispensing element 244, which may be multi-use or single-use. In other examples, different dispensing elements may be part of the dispensing device 230, wherein the dispensing elements may include but are not limited to spray dispensers, meter drug dispensers, liquid medium dispensers, gel dispensers, or sputter coating dispensers. Additionally other modification tools to modify the dispensed structural material and/or the biological material such as a puncturing tool, blade, rotating screw, laser cutter, pressurized sterile air, membrane dispensers (for dispensing membranes, fleeces, thin films, and shape-memory polymers), electrospinning fiber/nanofiber dispensers, dispensers for fluorescence or DNA identification tagging, or other tools may be attached to the dispensing device 230 for modifications of the printed object. The use of these post-printing modification tools for surface modification and the creation of internal pathways within the printed three-dimensional structures are described in U.S. patent application Ser. No. 14/680,180, which is incorporated herein by reference.

In this example the multi-use structural material dispensing element 232 dispenses a structural material 234, which may exemplarily be a thermoplastic material. The structural material 234 may move through an internal tube (not shown) to a heating element (not shown) and be dispensed through a narrow dispensing tip 240. An operator may control the temperature of the dispensing of the structural material 234. Further, the operator may control the flow of the material 234 through a plurality of controlling devices such as material dispense and retraction buttons 238 and a material selector switch 236, which selects which material from a plurality of materials should be dispensed by the dispensing device 230 when dispensing elements 262 and 244 are connected.

The multi-use structural material dispensing element 232 may use an attachment mechanism 242, e.g. a snap mechanism, to attach to a corresponding attachment mechanism 258 on the pipette liquid dispensing element 244.

The pipette liquid dispensing element 244 may comprise a plunger button 246, a volume adjustment knob 250, a volume indicator display 252, a tip ejector button 248, a tip holder 254, and a disposable pipette tip 256. The pipette liquid dispensing element 244 may contain an internal piston assembly (not shown) with a barrel, shaft, spring, and O-ring. The pipette liquid dispensing element 244 may be utilized for dispensing of a meter volume of a drug or chemical product or for the dispensing of liquid media or other growth-promoting fluids onto the printed object.

The pipette liquid dispensing element 244 may use an attachment mechanism 260, e.g. a snap mechanism, to attach to a corresponding attachment mechanism 270 on the single-use biological material dispensing element 262.

The single-use biological material dispensing element 262 may be constructed of sterilizable materials and may be sterilized utilizing a validated method, such as gamma irradiation, autoclaving, and/or chemical sterilization. In this example the single-use biological material dispensing element 262 may comprise a printer body which encloses a plurality of components. Furthermore, it may include at least one physical aseptic connector that may comprise two or more components, such as an OPTA® connector with a tubing to connect to an external sterile feed source of cells, media, and/or other biological materials, as well as a tubing component that transports the sterile feed material from the aseptic connection to an internal tubing (not shown).

The internal tubing (not shown) may run the length of the printer body until a dispensing tip 268 at one end. The dispensing tip 268 may comprise a plurality of shapes to alter the dispensing profile of the dispensed material, such as slow and focused or sprayed over a defined area or pattern. A vent filter 266, such as an integrity-testable, sterilizing-grade vent filter, may be utilized to properly vent the internal tubing (not shown) as it fills with material. The movement of the material through the single-use biological material dispensing element 262 may be provided by an external source such as a pneumatic pressure source, a pump, or an electric motor. Alternatively a pump, electric motor, and/or pneumatic pressure source may be internal to the dispensing device 230.

FIG. 3B is a side view of the dispensing device 230' where the plurality of connectable dispensing elements are in the connected state. In this example the multi-use structural material dispensing element 232', the pipette liquid dispensing element 244', and the single-use biological material dispensing element 262', are connected utilizing their respective attachment mechanisms. The attachment mechanisms may bring the pipette liquid dispensing element 244', the single-use biological material dispensing element 262' and the multi-use structural material dispensing element 232' in communicative contact with one another, wherein the connection may establish an electrical, mechanical, and/or fluid communication. Between each of the plurality of dispensing elements within the dispensing device 230' there may be thermal barriers (not shown) to prevent thermal energy transfer from negatively affecting the dispensing elements 244 and 262. The dispensing device 230' in the connected state may contain an ergonomically-molded handgrip on the material dispensing element 232', the pipette liquid dispensing element 244', the single-use biological material dispensing element 262', or across all elements for the comfort of the operator using the device.

In the connected configuration of the dispensing device 230', the material selector switch 236' may change the dispensing element selected, such as to either the pipette liquid dispensing element 244' or the single-use biological material dispensing element 262', in order to allow the operator to control the flow of material utilizing the material dispense and retraction buttons 238. The pipette liquid dispensing element 244' may utilize either the material dispense and retraction buttons 238 or the pipette plunger button 246 on the dispensing element itself, depending on which is more comfortable for the operator to operate. The dispensing tips 240, 254, 268 of their respective dispensing elements are sufficiently spaced to prevent overlapping or spraying onto another element, such as a spray coating liquid from dispensing element 244' coming into contact with the heated dispensing tip of the structural material dispensing element 232'.

The single-use biological material dispensing element 262' may be connected to a biological feed source 272 via at least one aseptic connection 264'. The aseptic connection 264' may be made using an aseptic connector such as an OPTA® connector and/or other physical aseptic connector, and/or may be achieved by thermowelding a tubing length of thermoweldable tubing to the feed assembly for a sterile connection with the biological feed source.

FIG. 3C is a side view of a dispensing device 280 where the multi-use structural material dispensing element 282 is attached to a thermal barrier 286 to prevent a heating element as discussed in the previous examples from negatively affecting the biological material within the single-use biological material dispensing element 284. The thermal barrier 286 may be formed in such a way that it provides communicative contact between the multi-use structural material dispensing element 282 and the single-use biological material dispensing element 284 through the attachment mechanism (not shown). The thermal barrier 286 may extend down to the dispensing tips 288, 289 to prevent any negative heating effects from the heating element during dispensing of structural material from dispensing tip 288 and the dispensing of biological material from dispensing tip 289.

FIG. 3D is a side view of a dispensing device 290 where the multi-use structural material dispensing element 292 is attached to a spacer element 296 to prevent a heating element as discussed in the previous examples from negatively affecting the biological material within the single-use biological material dispensing element 294. The spacer element 296 may be formed in such a way that it provides communicative contact between the multi-use structural material dispensing element 292 and the single-use biological material dispensing element 294 through the attachment mechanism (not shown). The spacer element 296 may only partially extend along the lengths of the dispensing elements 292, 294 to leave a gap between the dispensing tips 298, 299 where airflow from the workspace may prevent any negative heating effects from the heating element during dispensing of structural material from dispensing tip 298 and the dispensing of biological material from dispensing tip 299.

As discussed with reference to FIGS. 1A to 3D, the structural material dispensing element may comprise a temperature-regulating element such as a heating element. Additionally or alternatively, other temperature-regulating elements, such as a cooling element and a warming element, may be comprised in the dispensing device in order to regulate the temperature of the material to be dispensed. In one example, thermoregulation may be accomplished by one or more tubing lines in the dispensing device filled with thermally-regulated fluid. The thermally-regulated tubing lines may be filled, properly vented, and recirculated using an external pump and/or pneumatic pressurized source. The temperature regulation device for the fluid may be an external device that heats and/or cools the thermally-regulated fluid within a container and recirculates the fluid through the thermally-regulated tubing lines. In another example, thermoregulation may be accomplished by means of a single-use chemical temperature-regulating element, which may use an exothermic and/or endothermic chemical reaction for a single-use thermoregulation of the material to be dispensed. FIGS. 4A-4C shows examples of a handheld dispensing device comprising one or more temperature-regulating elements.

FIG. 4A is a side view of a single-use dispensing device 300 consisting of a printer body 302 that encloses a plurality of components manufactured from sterilizable materials and may be sterilized utilizing a validated method, such as gamma irradiation, autoclaving, and/or chemical sterilization. In this example, the dispensing device 300 may comprise a structural material dispensing element that dispenses material out of dispensing tip 312 and a biological material dispensing element that dispenses material out of dispensing tip 318. In other words, the dispensing elements are permanently connected and may be formed together. The single-use dispensing device 300 may contain an ergonomically-molded handgrip for the comfort of the operator using the device.

The structural material dispensing element of the dispensing device 300 may utilize a structural material 304 such as a low melting point thermoplastic material, which has a lower melting point then the plastic materials used for the printer body 302 and other internal components within the dispensing device 300. In other examples the structural material may consist of hydroxyapatite (HA), collagen, fibrin, hydrogels, chitosan, hyaluronic acid, sugars, gels, powders, or other structural materials that do not require heating beyond the melting point temperatures of the plastic materials used for the printer body 302 and other internal components within the dispensing device 300.

The structural material 304 may be inserted into the top of the structural material dispensing element portion of the dispensing device 300 and the dispensing speed may be determined by a feed motor (not shown) that has a plurality of gears (not shown) to control the movement of the thermoplastic structural material. In this example in which the whole dispensing device is single-use, the feed motor (not shown) may be driven by an external pneumatic/hydraulic pressure source attached to a fluid drive and thermoregulation connector 306.

In one example a pneumatic pressure source may be connected to the fluid drive and thermoregulation connector 306. In this case, the waste air, after running through the feed motor (not shown), may simply bleed the pressure off through the filter 305 in a direction away from the printed object or the filter may be connected to a length of tubing that removes the compressed air in excess away from the work area. In another example, a hydraulic pressure source may be connected to the fluid drive and thermoregulation connector 306. In this case, the waste fluid pressure after running through the feed motor (not shown) may use a tubing line to drain the compressed fluid away from the work area or to recover the fluid in a container (not shown) where it can be pressurized and recirculated through the device.

The structural material 304 may move through an internal tube (not shown) to a single-use heating element (not shown), which is described in more detail below with reference to views FIGS. 4B and 4C.

The single-use biological material dispensing element of the dispensing device 300 may be connected to a biological feed source via at least one aseptic connection 314. A vent filter 316, such as an integrity-testable, sterilizing-grade vent filter, may be utilized to properly vent the internal tubing (not shown) as it fills with material. The aseptic connection 314 may be made using an aseptic connector such as an OPTA® connector and/or other physical aseptic connector, and/or may be achieved by thermowelding a tubing length of thermoweldable tubing to the feed assembly for a sterile connection with the biological feed source.

An operator may control the dispensing of the structural and biological materials through dispense and retraction buttons 310 and a material selector switch 308, that may switch from dispensing the structural material to dispensing the biological material. In this example the controls may regulate the direction and force of the pneumatic/hydraulic pressure that controls the flow of materials within the single-use device 300.

FIG. 4B is a side view of a single-use dispensing device 320 comprising a fluid temperature control mechanism. The single-use dispensing device 320 may be a possible embodiment of the single-use dispensing device 300.

The single-use dispensing device 320 may comprise a printer body 322 that encloses a plurality of components manufactured from sterilizable materials and may be sterilized utilizing a validated method, such as gamma irradiation, autoclaving, and/or chemical sterilization.

The device 320 may comprise internal recirculation channels within a thermal regulating assembly 333 to transfer fluid for heating and cooling elements internal to the dispensing device 320. The individual fluid-conducting elements may be connected through a single connection, such as the fluid drive and thermoregulation connector 306 as shown in view 'A', to align and connect each of the individual tubing lines. The tubing lines may be segregated and insulated from one another to prevent the excess heat or cooling to negatively impact the temperature of a nearby temperature controlled tubing line. The tubing lines may comprise at least one of a fluid line 330, a heated tubing line 340, a cooled tubing line 346 and a warm tubing line 366, which will be described in more detail in the following.

Exemplarily, a structural material dispensing element 324 may comprise a structural material 326, a feed motor 328, a venting filter 332, internal tubing 334, a heating element 336, a cooling element 342, and a dispensing tip 348. The feed motor 328 may be driven by an external pneumatic pressure source attached to the fluid line 330. The waste air, after running through the feed motor 328, may simply bleed the pressure off through the venting filter 332 in a direction away from the printed object or the venting filter 332 may be connected to a length of tubing that removes the excess compressed air away from the work area.

The feed motor 328 may turn a plurality of gears that feed the structural material 326 into the internal tubing 334 to the heating element 336. The heating element 336 may comprise an assembly that circulates a heated fluid, such as heated sterile filtered water, glycol, and/or steam, from an external temperature-regulated fluid source through the heated tubing line 340. The heated tubing line 340 may be connected to an internal heating recirculation loop 338 that may be insulated to protect the internal components and other temperature-controlled fluid lines from being negatively affected by the elevated temperatures. The heating element 336, the heated tubing line 340, and the internal heating recirculation loop 338 may be made from high-melting-point plastics and/or metal components to resist deformation and/or promote thermal transfer during the recirculation of heated fluid to melt and dispense the structural material 326.

The single-use dispensing device 320 may be pre-sterilized and provided without any fluid present in the fluid tubing lines. The tubing lines may then be filled with thermally-regulated fluid prior to use. The thermally-regulated tubing lines may be filled, properly vented, and recirculated using an external pump (not shown) and/or pneumatic pressurized source (not shown). The temperature regulation device may be an external device that heats and/or cools the thermally-regulated fluid within a container and recirculates the fluid through the thermally-regulated tubing lines within the dispensing device 320.

In some instances the structural material 326 may be partially cooled after it passes through the heating element 336 to achieve the desired dispensing rate and consistency of the structural material 326 prior to it being dispensed from the structural material dispensing tip 348, particularly if the temperature regulation of the heating element using a heated fluid is not tightly controlled. The cooling element 342 may comprise an assembly that circulates a cooling fluid, such as cooled, cold, or chilled sterile filtered water, brine, glycol, and/or air, from an external temperature-regulated fluid source through the cooled tubing line 346. The cooled tubing line 346 may be connected to an internal cooling recirculation loop 344 that may be insulated to protect the internal components and other temperature controlled fluid lines from being negatively affected by the cool temperatures. The cooling element 342, the cooled tubing line 346, and the internal cooling recirculation loop 344 may be made from plastics and/or metal components.

Temperature sensors may be embedded into the heating and cooling elements 336, 342 to provide feedback to a computer control board and/or an operator on the dispensing conditions within the dispensing device 320. A biological material dispensing element 356 may contain a thermal barrier to prevent the heating element 336 and/or the cooling element 342 and internal thermal fluid control lines 338, 344 from negatively impact the dispensing of the biological materials.

The biological material dispensing element 356 may contain a warming element 364 to maintain the cells and/or biological material at a consistent temperature, such as incubation temperature 37° C., during dispensing. The warming element 364 may comprise an assembly that circulates a warm fluid, such as warm sterile filtered water, brine, glycol, and/or air, from an external temperature-regulated fluid source through the warm tubing line 366. The warming tubing line 366 may be connected to an internal warming recirculation loop 365 that may be insulated to protect the internal components and other temperature controlled fluid lines from being negatively affected by the warm temperatures. The internal warming recirculation loop 365 may be positioned so that the tubing lines pass through the thermal barrier 354. The warming element 364 may be positioned so that it provides consistent warming and thermal transfer over the entire length of an internal tubing 362 prior to dispensing out of a biological material dispensing tip 368.

The biological material dispensing element 356 may be connected to a biological feed source via at least one aseptic connection 358. A vent filter 360, such as an integrity-testable, sterilizing-grade vent filter, may be utilized to properly vent the internal tubing 362 as it fills with material. The aseptic connection 358 may be made using an aseptic connector such as an OPTA® connector and/or other physical aseptic connector, and/or may be achieved by thermowelding a tubing length of thermoweldable tubing to the feed assembly for a sterile connection with the biological feed source.

An operator may control the dispensing of the structural and biological materials through dispense and retraction buttons 350 and a material selector switch 352 that may switch from dispensing the structural material 326 to dispensing the biological material. In this example the controls may regulate the direction and force of the pneumatic pressure that controls the flow of materials within the single-use device 320.

FIG. 4C is a side view of a single-use dispensing device 370 comprising a plurality of single-use chemical heating elements. The single-use dispensing device 370 may be a possible embodiment of the single-use dispensing device 300.

The single-use dispensing device 370 may comprise a printer body 372 that encloses a plurality of components manufactured from sterilizable materials and may be sterilized utilizing a validated method.

The device 370 may comprise a single-use chemical heating element, which is based on mechanisms such as the exothermic oxidation of iron when exposed to air, or a re-usable chemical heater element, which is based on mechanisms such as the exothermic crystallization of supersaturated solutions.

A structural material dispensing element 374 of the device 370 may comprise a structural material 376, a feed motor 378, a venting filter 380, internal tubing, a two-chamber chemical heating element 382, 384, and a dispensing tip. The feed motor 378 may be driven by an external pneumatic pressure source attached to a fluid line 383. The waste air, after running through the feed motor 378, may simply bleed the pressure off through the venting filter 380 in a direction away from the printed object or the venting filter 380 may be connected to a length of tubing that removes the excess compressed air away from the work area.

The feed motor 378 may turn a plurality of gears that feed the structural material 376 into the internal tubing to the two-chamber heating element 382, 384. The two-chamber heating element 382, 384 may comprise two different chemical materials, such as calcium oxide and water, which are kept separated by a seal 388. Exemplarily, when the seal 388 is removed by an operator by pulling on the tape containing the seal 388 from a slot 386 in direction 390, the two separated chemicals in the two-chamber heating element 382, 384 mix. The mixing causes an exothermic reaction resulting in the heating element temperature to increase. In other examples, a single-stage chemical heating element may be utilized (not shown), where the seal 388 may be removed to expose the single-stage element to air for the exothermic oxidation of iron as the heating source. The chemical heating method utilized must have sufficient heat and time duration to provide consistent thermal energy for melting the structural material 376 planned for use.

A biological material dispensing element 392 of the device 370 may contain a thermal barrier 404 to prevent the chemical heating element 382, 384 from negatively impacting the dispensing of the biological materials. The biological material dispensing element 392 may include two-chamber warming element 396, 394 that may comprise two different chemical materials kept separated by a seal 400. Exemplarily, when the seal 400 is removed by an operator by pulling on the tape containing the seal 400 from a slot 398 in direction 402, the two separated chemicals in the two-chamber warming element 396, 394 mix, causing an exothermic reaction resulting in the warming element temperature to increase. The warming element chamber 394 may use a matrix and/or gel to moderate and control the exothermic reaction to prevent excessive heat from damaging the biological materials as they move through the internal tubing. Alternatively a supersaturated solution of sodium acetate may utilize exposure to a metal disc, by removing seal 400, which helps initiate nucleation and the crystallization generating heat from the exothermic reaction.

Temperature sensors may be embedded into the heating and warming elements to provide feedback to a computer control board and/or an operator on the dispensing conditions within the dispensing device 370. A plurality of heating and warming element chambers may be utilized to keep the heating over a defined duration depending on the length of time it takes to complete the processing of the material into a printed object. Alternatively the operator may remove the used chemical heating elements and replace them with new elements such as in a replaceable cartridge configuration. Alternatively the operator may dispose of the previous dispensing device 370 and connect it to a new dispensing device if the chemical heating elements did not last for the duration required to complete the printing of the object.

Both the structural material and the biological material dispensed by the dispensing devices described above may require some kind of pre-processing prior to being dispensed. Examples of pre-processing may include but are not limited to mixing, selecting, changing the concentration of the material. FIGS. 5A-5D show examples of dispensing elements comprising different mechanisms for pre-processing of the material to be dispensed. Any of the dispensing devices described with reference to the previous figures may comprise one or more of these dispensing elements.

FIG. 5A is a side view of an single-use biological material dispensing element 500 containing a mixing device that comprises a shaft with one or a plurality of impellers 502, which may connect to an external magnetic or geared shaft connection 504 containing a seal. The shaft connection may be the mechanism to drive the rotation of the shaft and the impellers 502.

An internal tubing for the biological material may contain a plurality of baffles 506 to aid in the mixing and dispensing of biological materials aseptically received from a feed source 508. The mixing device and baffles 506 may allow for proper mixing and uniformity of a heterogeneous material, for easier dispensing of a viscous material, and/or for promoting the dispensing of either denser or less dense materials such as dispensing cells while removing cell debris. Additionally or alternatively a sparger (not shown) and/or a microsparger (not shown) with a sterile air connection (not shown) may be utilized for proper aeration and mixing of the biological material prior to dispensing. Additionally, the biological materials may be combined with gels, hydrogels, alginates, or thickening agents to aid in the precision dispensing and attachment to structures and/or scaffolding. The thickening agents may be added through an upstream connection of the feed material or within the internal tubing of the single-use biological dispensing element 500 via an alternate aseptic connector (not shown). The thickening agents may require vigorous mixing utilizing the mixing device to achieve the proper consistency for dispensing.

FIG. 5B is a side view of a single-use biological dispensing element 510 containing one or a plurality of internal roller elements 512 that may be connected to an external drive mechanism and/or a drive mechanism of a connected multi-use structural material dispensing element through magnetic or geared connections 516. The drive mechanism (not shown) may utilize a geared shaft, a magnetic assembly, a pneumatic air source, and/or a hydraulic fluid source to drive the internal roller elements 512. The internal roller elements 512 may promote mixing and dispensing of biological materials aseptically received from the feed source 514. The roller elements may contain a plurality of protrusions or impeller blades at different pitches and lengths to assist with moving or selecting material with defined sizes prior to dispensing. The internal roller elements 512 may additionally promote the dispensing of specific materials such as cells that have a certain defined shape and density.

FIG. 5C is a side view of a single-use biological dispensing element 520 containing a one or a plurality of internal membrane elements 522 for the concentration or dilution of the biological material prior to dispensing. The internal membrane elements 522 may be incorporated into an internal tubing and be utilized to remove fluid material from the biological material prior to dispensing using an external connection 524 and a vacuum force 526. The internal membrane elements 522 may be sized to properly remove selected materials and to have the force of the removal controlled to protect the remaining biological materials, such as for the removal of fluids for concentration while maintaining healthy cells for dispensing. In other examples, sterile fluid may be injected into the dispensing element 520 through a sterilizing grade membrane element to dilute the biological materials aseptically received from a feed source 528 to a certain concentration. Examples are for reducing the trypsin concentration used to remove cells from adherent plates, or to provide a chemical aid for promoting the adhering of the cells or biological material to the printed structural material. A biological material dispensing tip 530 may contain a Luer Lock connection or other attachment mechanism to attach to a sized filter device 532 that may be placed just prior to dispensing the biological material. The sized filter device 532 may provide sterilizing-grade fluid, thereby removing any potential bacterial contamination while allowing small biological materials such as proteins to pass through. The plurality of internal membrane elements 522 and the sized filter device 532 may be integrity testable.

FIG. 5D is a side view of a single-use biological dispensing element 540 containing a single-use cell concentrator device 542, such as a Hydrocyclone® for the controlled cell retention and concentration prior to dispensing. The single-use cell concentrator device 542 may be aseptically connected to a biological material feed source 544 with two tubing lines. The material is concentrated by means of the flow of material within the interior of the cell concentrator device 542 through sedimentation in a centrifugal field, which is similar to centrifugation but with no movable parts. The cells are concentrated and enter the internal tubing via a concentrated underflow connection 546 of the single-use biological material dispenser 540, while the cell debris and used media are removed via an overflow connection 548. In other examples, the opposite products may be desired and the single-use concentrator device 542 connections may be changed to supply the single-use biological material dispenser 540 with tubing line 548 while discarding the material from the concentrated underflow connection 546. In other words, the cells may be discarded and the used media containing the desired biological material may be harvested and used within the internal tubing of the single-use biological material dispenser 540.

A handheld dispensing device may be connected to a biological material source via an aseptic connection assembly, which may comprise, but is not limited to, any combination of a filtration train, a surge vessel container, tubes, a fermenter, a cross flow assembly, a membrane adsorber, a centrifugation apparatus, and an incubator.

FIG. 6 shows an example of a system 600 comprising a handheld dispensing device 624 and a biological material source 602. The handheld dispensing device 624 may comprise the features of one or more of the dispensing devices described with reference to FIGS. 1A to 5D.

The sterilized printing and feed material system 600 may comprise the biological material source 602 such as a single-use bioreactor, which may be e.g. a microbioreactor, which is connected to a filtration train via an aseptic connector 604. The filtration train (or filter train) may comprise one or a plurality of filters including but not limited to a depth filter 606, a pre-filter 608, and a sterilizing-grade filter 610. The filter train is optional if cells and/or cell products that would be captured within the filters are the desired biological feed material for printing.

The filter train may be connected to a surge vessel container 614 exemplarily with an additional aseptic connector (not shown) or may be sterilized as a complete assembly. The surge vessel container 614 may fill with the material filtered from the bioreactor 602, which can be driven by a constant pressure or a constant flow source. A sterilizing grade vent filter 616 may allow the surge vessel container 614 to vent during filling. After the filtration process is complete or the surge vessel container 614 is full, a valve 612 to the filter train may be closed and a regulated compressed air line 618 may be attached to the sterilizing grade air filter 616.

The pressure drives the liquid up a dip tube 620 and into a tubing piece which is connected via an aseptic connector 622 to the dispensing device 624. The material from the surge vessel container 614 can be concentrated utilizing a cell retention and concentration device, such as a gamma irradiatable Hydrocyclone (not shown). Additionally, the biological material may be connected to a sensor device and/or have an integrated sensor device for cell counting and cell viability. The sensor device for cell counting and cell viability may include but is not limited to a nucleocounter, a flow cytometer, and/or a radio frequency impedance device, preferably a BioPat® ViaMass Sensor unit.

An operator may utilize the dispensing device 624 within a clean environment with sufficient airflow to prevent contamination, such as a laminar flow hood or a biological safety cabinet, or within a sterilized environment such as an isolator, glovebox, or sterile chamber. The operator may precisely control the dispensing of the structural material onto a printing tray or container such as a multi-well plate 626 using the structural material dispensing element of the dispensing device 624 to form a scaffolding or structure to support the biological materials. The processed biological material may be precisely deposited using the biological material dispensing element of the dispensing device 624 onto the structural material within the multi-well plate 626. The 3D printed object within the multi-well plate 626 is formed by layer-by-layer additive printing of structural material from the dispensing device 624 that is manually operated. After the printing of the structural material, the biological material may be added and the printed object within the multi-well plate 626 may be filled with a nutrient fluid media. The multi-well plate 626 may be covered, removed from the printing environment, and incubated within an incubated container for further study, sampling, and/or evaluation.

Figure 7:
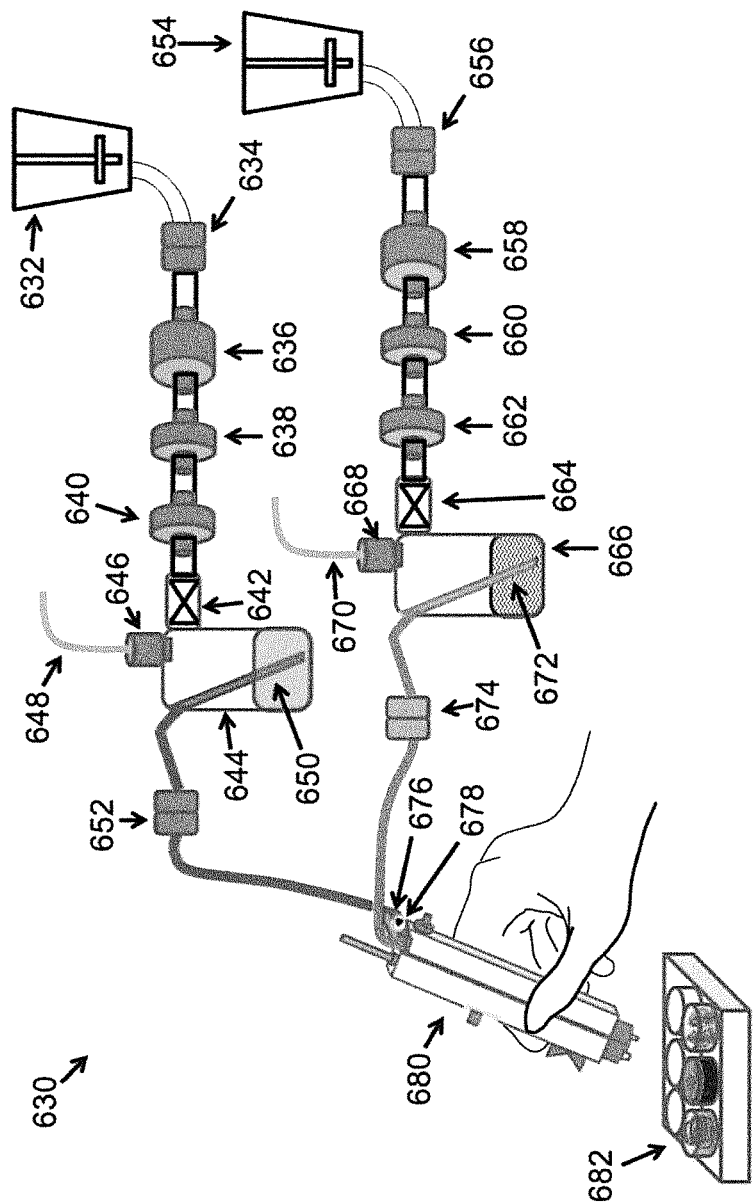
FIG. 7 shows an example of a system comprising a handheld dispensing device and two biological material sources.

FIG. 7 shows an example of a system 630 comprising a handheld dispensing device 680 and a plurality of biological material sources, such as two single-use bioreactors 632, 654. The handheld dispensing device 680 may comprise the features of one or more of the dispensing devices described with reference to FIGS. 1 to 5.

The sterilized printing and feed material system 630 may comprise at least two single-use bioreactors 632, 654 that are connected to their respective filtration assemblies via aseptic connectors 634, 656. The filtration train for the first single-use bioreactor 632 may comprise one or a plurality of filters including but not limited to a depth filter 636, a pre-filter 638, and a sterilizing-grade filter 640. The filtration train for the second single-use bioreactor 654 may comprise one or a plurality of filters including but not limited to a pre-filter 658, a mycoplasma retentive filter 660, and a virus retentive filter 662. The filter train assemblies are optional if cells and/or cell products that would be captured within the filters are the desired biological feed material for printing.

The filter train assemblies may be connected to surge vessel containers 644, 666 exemplarily with the use of additional aseptic connectors (not shown) or may be sterilized as complete assemblies. The surge vessel containers 644, 666 may fill with the material processed from the single-use bioreactors 632, 654, which can be driven by a constant pressure or a constant flow source. Sterilizing grade vent filters 646, 668 may allow the surge vessel containers 644, 666 to vent during filling. After the filtration processes have completed or the surge vessel containers 644, 666 are full, valves 642, 664 to the filter train assemblies may be closed and regulated compressed air lines 648, 670 may be attached to sterilizing-grade air filters 646 and 668 respectively.

The pressure drives the liquid up the dip tubes 650, 672 and into tubing pieces that are connected via aseptic connectors 652, 674 to the dispensing device 680. A plurality of feed sources of biological materials may be aseptically connected to a manifold 676 on the dispensing device 680. A selection valve 678 located on the manifold 676 may be utilized to select the feed source to be connected to the interior tubing of the single-use biological material dispensing element during dispensing.

An operator may precisely control the dispensing of the structural material onto a printing tray or container such as a multi-well plate 682 using the structural material dispensing element of the dispensing device 680 to form a scaffolding or structure to support the biological materials. The processed biological material may be precisely deposited using the biological material dispensing element of the dispensing device 680 onto the structural material within the multi-well plate 682. The three dimensional printed object within the multi-well plate 682 is formed by layer-by-layer additive printing of structural material from the dispensing device 680 manually operated. After the printing of the structural material, the biological material may be added and the printed object within the multi-well plate 682 may be filled with a nutrient fluid media. The dispensing device 680 may dispense material into at least one well within the multi-well plate 682 from a single biological feed source such as the material originating from a single-use bioreactor 632 or the material originating from a plurality of single-use bioreactors 632, 654 may be dispensed within at least one well within the multi-well plate 682. The different feed sources may be dispensed by the operator onto different sections of the structural material or scaffolding to form a complete object. The multi-well plate 682 may be covered, removed from the printing environment, and incubated within an incubated container for further study, sampling, and/or evaluation.

FIG. 8 shows an example of a system 700 comprising a handheld dispensing device 742, a biological material source such as a single-use bioreactor 702, a centrifugation assembly 706 and a crossflow assembly 728. The handheld dispensing device 742 may comprise the features of one or more of the dispensing devices described with reference to FIGS. 1 to 5.

The sterilized printing and feed material system 700 may comprise a single-use bioreactor 702 connected to the centrifugation assembly 706 via an aseptic connector 704. The filtration train assembly may be connected to the centrifugation assembly 706 via an aseptic connector (not shown) and comprise one or a plurality of filters including but not limited to a depth filter 708, a pre-filter 710, and a sterilizing-grade filter 712. The filter train is optional if cells and/or cell products that would be captured within the filters are the desired biological feed material for printing.

The filter train assembly may be connected to a surge vessel container 716 exemplarily with an additional aseptic connector (not shown) or may be sterilized as a complete assembly. The surge vessel container 716 fills with the material filtered from the bioreactor, which can be driven by a constant pressure or a constant flow source. A sterilizing grade vent filter 718 may allow the surge vessel container 716 to vent during filling. After the filtration process is complete or the surge vessel container 716 is full, a valve 714 to the filter train may be closed and a regulated compressed air line 720 may be attached to the sterilizing grade air filter 718.

The pressure drives the liquid up a dip tube 722 and into a tubing piece which may be connected via an aseptic connector 722 to a pre-sterilized membrane adsorber 726. The membrane adsorber 726 may be a chromatographic membrane carrying functional groups for the reversible binding of biomolecules. The desired molecules can be captured with the membrane adsorber and eluted at a later time or undesirable molecules can be removed by membrane adsorption before further processing. The membrane adsorber 726 may be connected to a pre-sterilized cross flow assembly 728. The cross flow assembly 728 may comprise a plurality of microfiltration and/or ultrafiltration cassettes in varying sizes.

The cross flow assembly 728 may be connected to a surge vessel container 732 via an aseptic connector (not shown). The surge vessel container 732 fills with the material filtered and/or concentrated from the cross flow assembly 728, which may be driven by a constant pressure or a constant flow source. Additionally or alternatively, other common bioprocess processing methods of the biological material may occur, such as column chromatography, high performance liquid chromatography (HPLC), fast protein liquid chromatography (FPLC), and one of these other processes may fill the surge vessel container 732. A sterilizing grade vent filter 734 may allow the surge vessel container 732 to vent during filling. After the cross flow processing is complete or the surge vessel container 732 is full, a valve 730 to the cross flow assembly may be closed and a regulated compressed air line 736 may be attached to the sterilizing grade air filter 734.

The pressure drives the liquid up a dip tube 738 and into a tubing piece that may be connected via an aseptic connector 740 to the dispensing device 742. An operator may precisely control the dispensing of the structural material onto a printing tray or container such as a multi-well plate 744 using the structural material dispensing element of the dispensing device 742 to form a scaffolding or structure to support the biological materials. The processed biological material may be precisely deposited using the biological material dispensing element of the dispensing device 742 onto the structural material within multi-well plate 744. The 3D printed object within the multi-well plate 744 is formed by layer-by-layer additive printing of structural material from the dispensing device 742 manually operated. After the printing of the structural material, the biological material may be added and the printed object within the multi-well plate 744 may be filled with a nutrient fluid media. The multi-well plate 744 may be covered, removed from the printing environment, and incubated within an incubated container for further study, sampling, and/or evaluation. Additionally or alternatively the operator may dispense the biological material onto an alternate substrate, such as a membrane (not shown) and/or diagnostic strips (not shown). The dispensing device 742 may spray deposit proteins and/or other concentrated ultra-filtered materials onto the membranes strips for use in diagnostic analysis. Additionally other structural components may be added to the membrane strips by layer-by-layer additive printing of material from the dispensing device 742.

Figure 2:
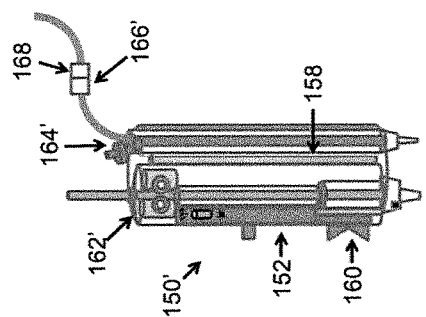
FIGS. 2A-2D shows an example of a handheld dispensing device comprising a body provided with at least one sleeve.
Figure 2:
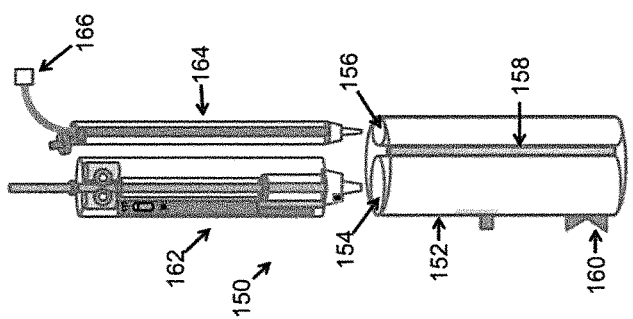
Figure 2:
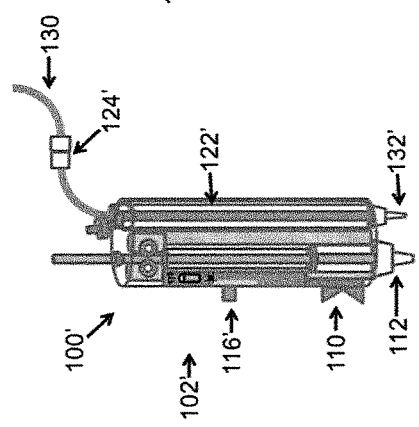
Figure 2:
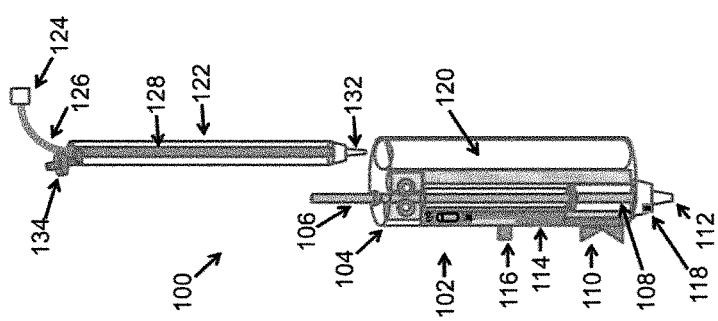
Figure 3:
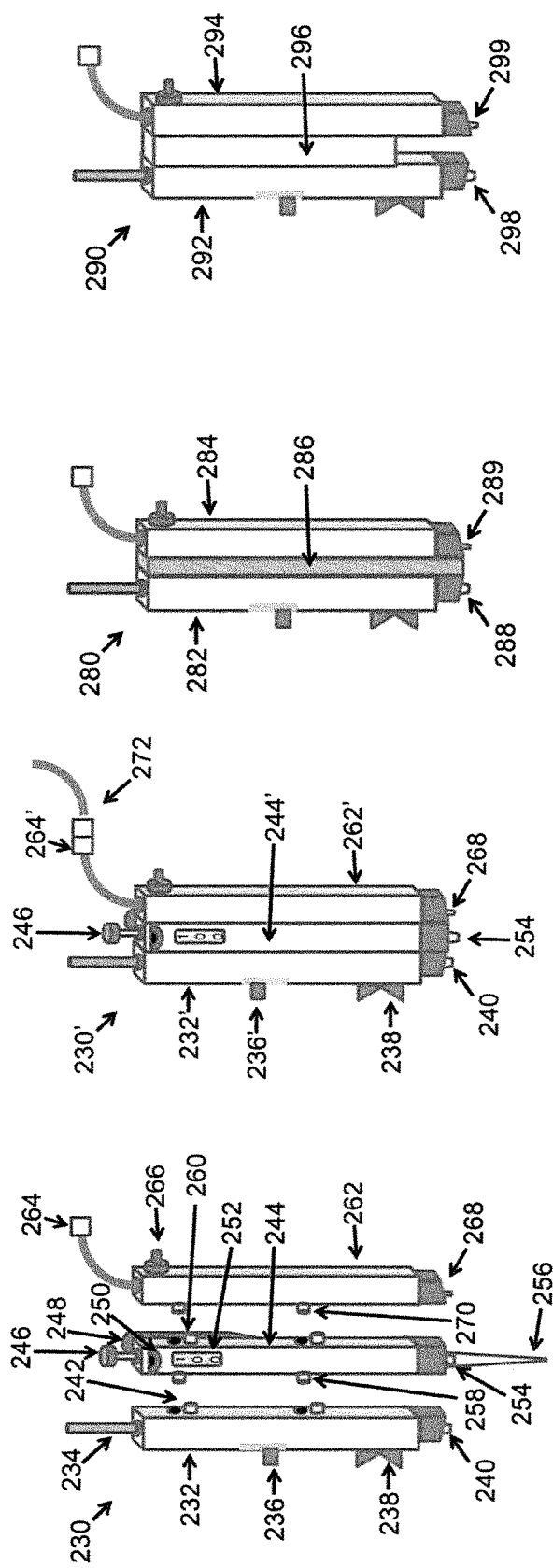
FIGS. 3A-3D shows other examples of a handheld dispensing device comprising an attachment mechanism.
Figure 4:
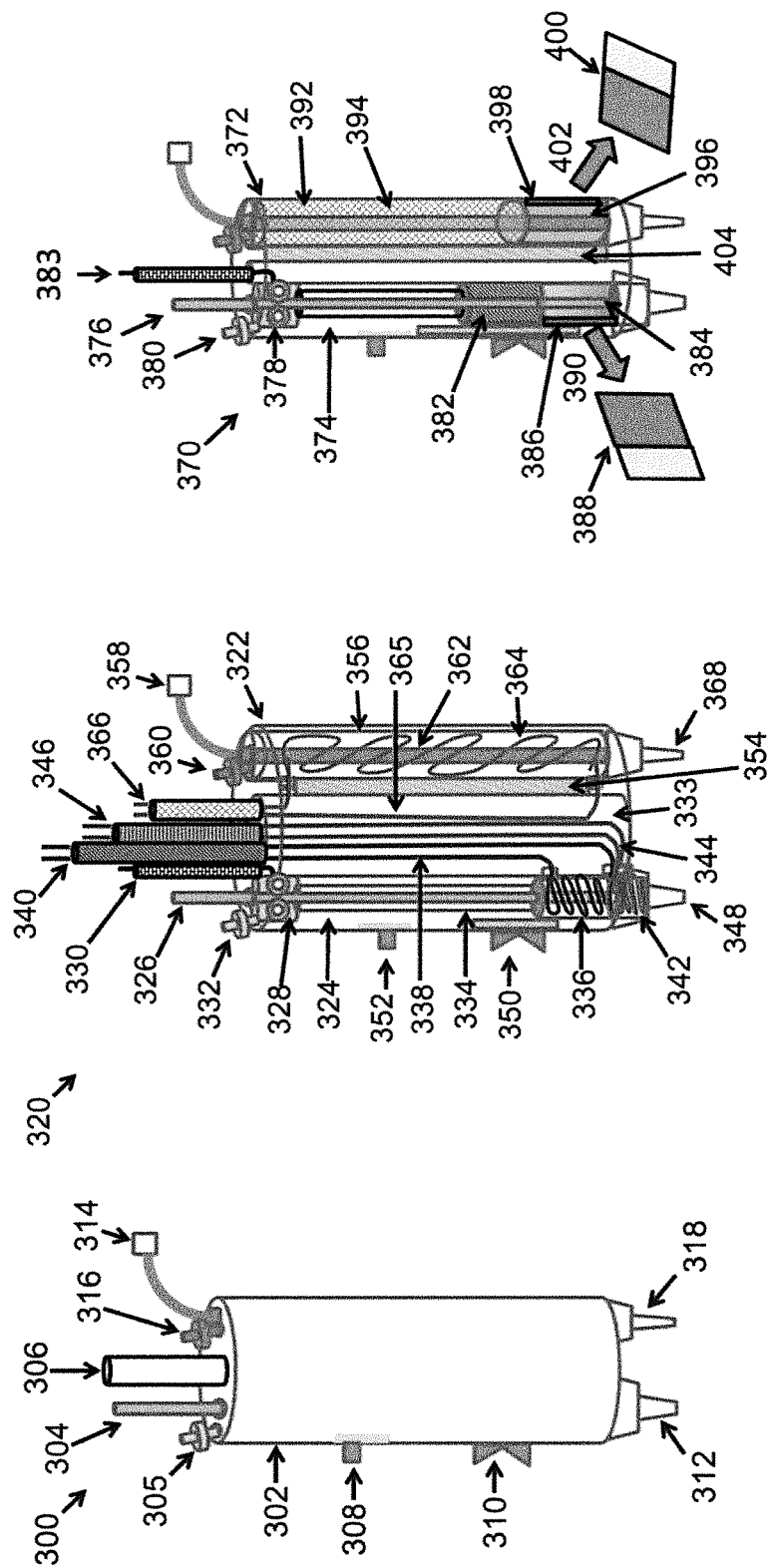
FIGS. 4A-4C shows examples of a handheld dispensing device comprising one or more temperature-regulating elements.
Figure 5:
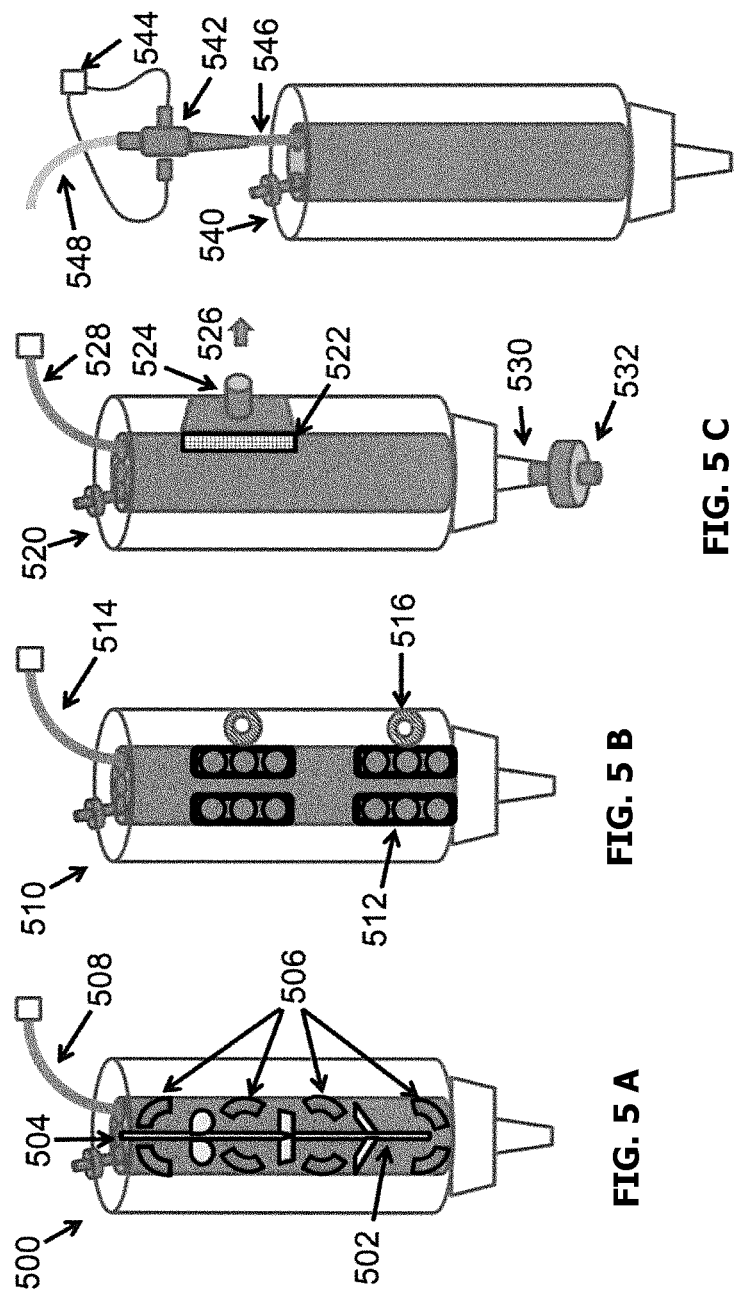
FIGS. 5A-5D shows examples of dispensing elements comprising different mechanisms.
Figure 6:
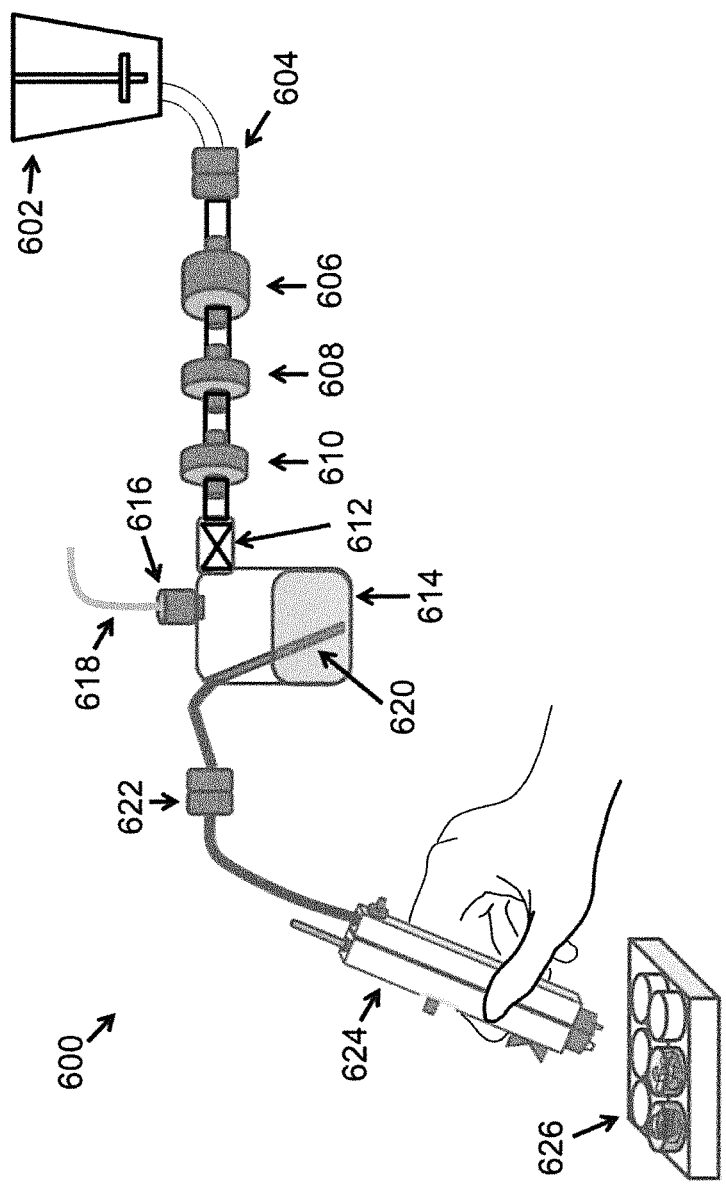
FIG. 6 shows an example of a system comprising a handheld dispensing device and a biological material source.

As described with reference to FIGS. 1 and 2, the dispensing device may comprise positional sensors. Generally, positional sensors may be formed within, connected to, or inserted within the dispensing device for tracking the orientation and movement in a three dimensional space. The dispensing device may additionally comprise other internal sensors to collect additional information on the dispensing process, such as volume dispensed or dispensing speed. Alternatively, data on the dispensing process of the dispensing device such as position, orientation, movement, materials dispensed, volume dispensed, and conditions may be tracked within a workspace using an external monitoring device. The data generated from the internal sensors and/or external monitoring device may be stored as a file in an internal memory storage device, an external memory storage device, a connected memory storage device, and/or a networked memory storage device. The stored data may be edited, e.g. scaled-up, and used to print a plurality of replicas of a 3D object within a large-scale 3D printer, such a single-use biological 3D printer.

FIG. 9 shows an example of an external monitoring setup for the monitoring of a handheld dispensing device 1010. The handheld dispensing device 1010 may comprise the features of one or more of the dispensing devices described with reference to the previous figures.

FIG. 9 shows a front view of an external monitoring system setup 1000 including an augmented reality system 1006 that comprises a camera and lighting array sensing device 1002 with a wired/wireless connection to a display device 1004. The camera and lighting array sensing device 1002 may contain one or a plurality of cameras, such as video cameras, depth cameras, infrared cameras, thermal cameras, or Light detection and ranging (LIDAR), etc. as well as one or a plurality of adjustable lights to fully illuminate the workspace for optimal tracking of markers. The camera and lighting array sensing device 1002 may monitor and image a workspace 1008, which may contain one or a plurality of identification markers.

The workspace 1008 may be within a clean environment with sufficient airflow to prevent contamination, such as a laminar flow hood or a biological safety cabinet, or within a sterilized environment such as an isolator, glovebox, or sterile chamber. The workspace 1008 may additionally be on a benchtop or desk in a non-sterile or non-clean environment for practicing printing a plurality of three dimensional objects following a defined protocol.

The one or more identification markers may identify objects within the workspace field of view and provide linked information on them, coded protocol identifiers to load a specific program of instructions from a database to be followed for printing a plurality of objects. The identification markers may for e.g. be static or variable augmented-reality markers. An augmented-reality marker may be a physical or virtual tag that provides unique identification information and positional information. A variable augmented-reality marker may have at least two states (e.g. it shows two different images) and the presentation of one of those states may be triggered by an operator's input or a computer product input, e.g. at a programmed interval. Coordinate markers 1022, 1024 may provide an augmented coordinate system 1026 where objects between the coordinate markers 1022, 1024 and within the field of view of the sensing device 1002 may be tracked based on the relative distance between the coordinate markers 1022, 1024, which may be viewed as an augmented image on the display device 1004 as described in U.S. Pat. No. 8,749,396 B2, which is incorporated herein by reference. The display device 1004 may be a monitor, screen, or projection display, or a wearable display such as a head mounted display device (HMD), an augmented reality display, a virtual reality display, or a mixed reality display device.

An operator 1012 may use the dispensing device 1010 to dispense structural materials and/or biological materials into a printer tray or dispensing container, which for example may be a multi-well plate 1020. The augmented reality system 1006 can precisely track the movement of the dispensing device 1010 within the workspace 1008 in three dimensions through the use of one or a plurality of light emitting diodes 1018, which may exemplarily be infrared light emitting diodes and wherein each infrared LED emits a different specific wavelength, and a variable marker 1016 both located on the dispensing device 1010. The variable marker 1016 on the dispensing device 1010 can change the presentation to the augmented reality system 1006 depending on the material selected to be dispensed, the initiation of dispensing, the rate of dispensing, the conditions of dispensing, and the volume of material dispensed. The augmented reality system 1006 may present an augmented display 1028 of a plurality of 3D virtual objects 1032, showing the material types, the material shapes, and the material volumes required to be dispensed into each well of the multi-well plate 1020 or printing tray in accordance with a defined protocol.

The augmented reality system 1006 may record the movement of the infrared LED 1018 as well as the location and presentation of the variable marker 1016 as a 3D wireframe diagram, which is a virtual line that tracks the movement of the marker in three-dimensional space over time, and compares the movements of the marker with a reference diagram within a pre-programmed tolerance, as described in U.S. Pat. No. 8,982,156 B2, which is incorporated herein by reference. As the variable marker 1016 changes its presentation to the augmented reality system 1006, the changes may be recorded on the wireframe diagram stored by the augmented reality system. The dispensing device 1010 may comprise one or a plurality of positional sensors 1014 including but not limited to motion sensors, orientation sensors, gyroscopic sensors, environmental sensors, cameras, depth sensors, magnetometers, accelerometers, proximity sensors, GPS devices, IMUs and internal or external positioning sensors. The information from the one or more orientation and positioning sensors of the dispensing device assembly 1010 may be communicated to the augmented reality system 1006 via a wired or wireless connection to provide additional real-time positional information for the augmented reality display 1004.

The augmented reality system 1006 may additionally provide a superimposed video and/or animation 1030 of the correct procedure and proper positioning of the dispensing device 1010 to physically print a 3D virtual object 1032. The procedure may be performed on the display 1004 so that the operator can follow the superimposed video and/or animation 1030 to correctly complete the proper procedures and the sequence for the performance of a work task. The superimposed video and/or animation 1030 may automatically speed up or slow down to mimic the speed and steps of the operator 1012 based on the infrared LED marker tracking, the variable marker tracking, the positional sensor tracking, or a combination thereof. Alternatively, the positional tracking information of the dispensing device 1010, the augmented display 1028 and the 3D virtual object 1032 to be printed may be displayed on a virtual reality display device (not shown) or mixed reality display device (not shown). The operator may be evaluated and graded by the software that tracks the movements and presentation of the variable markers within an operator-defined system for performing or following the proper technique for a predetermined task within the margin of error. If the operator meets a certain proficiency level, the augmented reality system 1006 may qualify the operator as meeting the requirements for performing the work task. This qualification can be the initial qualification for the operator or one of pre-programmed periodic qualifications, such as part of an annual re-training and evaluation.

The dispensing device shown in FIGS. 1 to 9 is a handheld dispensing device. However, such a dispensing device, i.e. with the same characteristics, may alternatively be controlled by a robotic control tool. According to one example, the robotic control tool may be manually controlled by an operator via a communication with an external control device maneuvered by the operator. According to another example, the robotic control tool may be controlled by an automatically-operated external control device and run a pre-programmed operation for printing. FIGS. 10 and 11 show examples of a dispensing system comprising a sterilizable chamber, a dispensing device and an external control device.

The dispensing system 800 shown in FIG. 10 may include a sterilizable chamber 802 that comprises at least one robotic arm assembly 804, a port 814 to connect the external control device 830 with the robotic arm assembly 804, and a transfer hatch 810 for the chamber 802. The chamber 802 may be within a clean environment with sufficient airflow to prevent contamination, such as a laminar flow hood or a biological safety cabinet, or within a sterilized environment such as an isolator, glovebox, or sterile chamber. In one example, the chamber 802 may be a pre-sterilized chamber containing the robotic arm assembly 804, a dispensing device 806 and a plurality of printing trays or containers such as multi-well plates 808. The dispensing device 806 may be a single-use assembly that has been sterilized along with the pre-sterilized chamber 802 or it may be sterilized separately using an alternative sterilization method from the sterile chamber and aseptically inserted utilizing an aseptic connection and insertion method (not shown).

Exemplarily, the robotic arm assembly 804 may utilize one or a plurality of actuators to control the positioning and movements of the dispensing device. The robotic arm assembly 804, including the plurality of actuators, may be made out of sterilizable (gamma irradiatable and/or autoclavable) plastic materials and rubberized seals. For example, the robotic arm assembly 804 may be controlled by utilizing an actuator to rotate a rotating base. The actuators may be driven by hydraulic, pneumatic, electric, or magnetically controlled methods (not shown). In one example, the movements of the robotic arm assembly 804 may be controlled via an external control device, which may be a manual controller operated by an operator external to the sterilized chamber 802.

The external control device 830 may utilize one or more hydraulic and/or pneumatic tubing lines 818 to move fluid through the port 814 into the actuators located on the robotic arm assembly 804 to control the movements. The tubing lines 818 may be filled with a sterile fluid through a filling assembly 820, wherein the fluid may apply hydraulic and/or pneumatic pressure. For example, the tubing lines may be filled with a sterile hydraulic fluid such as sterile filtered water. The sterile filtered water may enter into the robotic arm assembly 804 and the external control device 830 after sterilization and setup for use by an operator. The tubing lines to the internal robotic arm assembly 804 may be connected to the external filling assembly 820 and/or the external control device 830 utilizing an aseptic connector (not shown). Purified water may enter through a tubing line 824, pass through a sterilizing grade filter 826 and then enter into the filling assembly 820, which may serve as a manifold to completely fill each of the individual tubing lines 818. The interior of the tubing lines 818 may be cleared of air through a sterilizing grade vent filter 828 that allows the displaced air to vent to the atmosphere as it is displaced by sterile filtered water entering into the assembly. A valve 822 on the filling assembly 820 may be closed when the charging of the fluid lines has been completed. Additional sterile filtered water, other fluids, or in other examples air or gas may be added to the tubing lines 818 via the filling assembly 820 in case of leakage or loss of pressure.

The external control device 830 may be utilized to control the movements of the robotic arm assembly 804. The external control device 830 may be in the shape of the dispensing device 806 to simulate the movement and control of the device by the operator's hand 834. Alternatively the external control device 830 may be in the shape of a stylus or other minimalized simulant of the actual shape or design of the dispensing device 806, which provides movement and external control by the operator of the robotic arm assembly 804 internal to the sterile chamber 802.

A plurality of hydraulic and/or pneumatic pistons may be arranged as a piston assembly 836 and filled with fluid, wherein the pistons may be pushed and/or pulled by the operator. This movement of one of the pistons 836 may alter the movement of a seal internal to the piston and alter the displacement of the internal fluid, resulting in the movement of the corresponding pistons 812 on the robotic arm assembly 804. The movement is transmitted by the pressure of the fluid that moves through the tubing lines 818 into the sterile chamber 802.

A body 832 of the external control device 830 may contain all of the same buttons, switches, and displays as the dispensing device 806. A data cable 838 may transmit the data resulting from e.g. the pushing of a button or other inputs from the body 832 to the internal dispensing device 806 through the corresponding internal data cable 816. The data cables 816, 838 may provide data, power, and/or fluid communication to the internal dispensing device 806. Exemplarily, commands from the external control device may include but are not limited to the dispensing of material using the dispense and retraction buttons and the selection of which material (such as the structural material or the biological material) to dispense using the material selector switch. Conversely the internal data cable 816 may transmit sensor data and related information, such as position and orientation, from the internal dispensing device 806 to the corresponding data cable 838 on the external control device body 832.

The internal dispensing device 806 and/or the external control device 830 may contain a plurality of positional sensors including but not limited to motion sensors, orientation sensors, gyroscopic sensors, environmental sensors, cameras, depth sensors, magnetometers, accelerometers, proximity sensors, GPS devices, IMUs and internal or external positioning sensors. The information from the orientation and positioning of the biological three dimensional material dispensing device assembly 806 used by an operator can be saved into a file which may be utilized to print out a replica of the structural materials and biological materials in the exact same way as was manually printed utilizing a large-scale single-use biological 3D printer (not shown).

The purpose of the robotic arm assembly 804 is to move, manipulate, and dispense materials from the dispensing device 806 internal to the sterilized chamber 802 while the operator is operating comfortably outside of the sterilized chamber 802. Indeed, operating within an isolator or glovebox typically means dealing with bulky gloves, so that the fine controls of dispensing materials into a small printing tray or multi-well plate 808 may not be adequately maneuvered.

The transfer hatch 810 may be utilized to remove objects aseptically from the sterilized chamber 802 and/or to connect to additional sterilized chambers to form a more complex assembly. The robotic arm assembly 804 may additionally be utilized to move materials from one sterilized chamber to another through the connected transfer hatches 810.

FIG. 11 shows a dispensing system 850 comprising a chamber 852 that may include at least one robotic arm assembly 854, a port 865 to connect to an automated control assembly (or automatically-operated external control device) 880, and a transfer hatch 860 for the chamber 852. The chamber 852 may be within a clean environment with sufficient airflow to prevent contamination, such as a laminar flow hood or a biological safety cabinet, or within a sterilized environment such as an isolator, glovebox, or sterile chamber. Exemplarily, the chamber 852 may be a pre-sterilized chamber containing the robotic arm assembly 854, a dispensing device 856 and a plurality of printing trays or containers such as multi-well plates 858. The dispensing device 856 may be a single-use assembly that has been sterilized along with the pre-sterilized chamber 852 or it may be sterilized separately using an alternative sterilization method from the sterile chamber and aseptically inserted utilizing an aseptic connection and insertion method (not shown).

In one example the robotic arm assembly 854 may utilize a plurality of actuators to control the positioning and movements of the dispensing device 856. The robotic arm assembly 854, including the plurality of actuators, may be made out of sterilizable (gamma irradiatable and/or autoclavable) plastic materials and rubberized seals. Exemplarily, the robotic arm assembly 854 may be controlled by utilizing an actuator to rotate a rotating base. The actuators may be driven by hydraulic, pneumatic, electric, or magnetically controlled methods (not shown).

In one example the robotic arm assembly 854 may be controlled via the external automated control assembly 880. The external automated control assembly 880 may utilize a plurality of hydraulic and/or pneumatic tubing lines 866 to move pressurized fluid into an actuator assembly 862 located on the robotic arm assembly 854 to control the movements. The tubing lines 866 may be filled with a sterile fluid through a filling assembly 868, wherein the fluid may apply hydraulic and/or pneumatic pressure. For example, the tubing lines may be filled with a sterile hydraulic fluid such as sterile filtered water. The sterile filtered water may enter into the robotic arm assembly 854 and the external control device 880 after sterilization and setup for use by an operator. The tubing lines to the internal robotic arm assembly 854 may be connected to the external filling assembly 868 and/or the external control device 880 utilizing an aseptic connector (not shown). Purified water may enter through a tubing line 870, pass through a sterilizing grade filter 872 and then enter into the filling assembly 868, which may serve as a manifold to completely fill each of the individual tubing lines 866. The interior of the tubing lines 866 may be cleared of air through a sterilizing grade vent filter 874 that allows the displaced air to vent to the atmosphere as it is displaced by sterile filtered water entering into the assembly. A valve 876 on the filling assembly 868 may be closed when the charging of the fluid lines has been completed.

The automated control assembly 880 may be utilized to control the movements of the robotic arm assembly 854. Pluralities of hydraulic and/or pneumatic pistons arranged in a piston assembly 882 may be filled with fluid and the movements of the piston heads (not shown) may be automatically controlled with a processing device 886. A memory storage device 888 may store programs local to the automated control assembly 880 to control the movements of the robotic arm assembly 854 within a program for executing a printing of an object within the sterile chamber 852 using the robotic arm assembly 854 and the internal dispensing device 856. The processing device 886 may also process sensor data and alter the movements of the robotic arm assembly 854 based on the programs stored within the memory storage device 888.

A data cable 864 from the dispensing device 856 may connect to the automated control assembly 880 through data connection 884 to communicate data from the pre-programmed button pushes and settings at the automated control assembly 880 and send the data to the internal dispensing device 856 through the data cable 864. The data cable 864 may provide data, power, and/or fluid communication to the internal dispensing device 856 from the data connection 884 on the automated control assembly 880. Examples of commands from the automated control assembly 880 include but are not limited to the dispensing of material and the selection of which material to dispense. Conversely, the internal data cable 864 may transmit sensor data and related information, such as position and orientation, from the internal dispensing device 856 to the corresponding data connection 884 on the automated control assembly 880.

The automated control assembly 880 may additionally contain a wireless communication device 890 to import robotic arm assembly control protocols, wireless sensor data, through communication with an external network and/or a mobile device. The automated control assembly 880 may utilize the wireless communication device 890 to receive wireless data 902 from a wireless external input controller 894, which is a manual controller operated by an operator 895 external to the sterilized chamber 852. The wireless external input controller 894 may utilize positional information to send instructions to the automated control assembly 880 to control the movements of the robotic arm assembly 854 internal to the sterilized chamber 852. The wireless external control device 894 may be in the shape of the dispensing device 856 to simulate the movement and control of the device by the operator's hand 895. Alternatively the wireless external control device 894 may be in the shape of a stylus or other minimalized simulant of the actual shape or design of the dispensing device 856.

The wireless external control device 894 may contain a processing device 896, a memory storage device 898, a power device (not shown), such as an electrically-wired source or battery-powered source, and a communication device 900 to wireless communicate 902 the data from the movement of the wireless external control device 894 to the automated control assembly 880 or to another computer device. The wireless external control device 894 may contain a robotic arm assembly stand 892 that mimics the robotic arm assembly in the sterile chamber to provide the operator with the feeling of controlling the actual device.

The wireless external control device 894 may contain all of the same buttons, switches, and displays as the dispensing device 856. The commands from the wireless external control device 894, including the dispensing of material using the dispense and retraction buttons and the selection of which material to dispense using the material selector switch, may be wirelessly communicated 902 to the automated control assembly 880 or another computer device. Data from sensors in the actuators on the robotic arm assembly stand 892 may be communicated to the wireless external control device 894 for processing, memory storage, and external communication. The wireless data 902 from the wireless external control device 894 may be utilized for real-time printing within the sterile chamber 852 by the movements of the robotic arm assembly 854 and dispensing with the internal dispensing device 856. Alternatively the wireless data 902 from the wireless external control device 894 may be stored in a memory device 888, 898 as an object print file for execution at a later time.

The internal dispensing device 856 and/or the wireless external control device 894 may contain a plurality of positional sensors including but not limited to motion sensors, orientation sensors, gyroscopic sensors, environmental sensors, cameras, depth sensors, magnetometers, accelerometers, proximity sensors, GPS devices, IMUs and internal or external positioning sensors. The information from the orientation and positioning of the dispensing device 856 or the wireless external control device 894 used by an operator can be saved into a file which may be utilized to print out a replica of the structural materials and biological materials in the exact same way as was manually printed utilizing a large-scale single-use biological 3D printer 910. Additionally or alternatively the data communicated 902 from the positional sensors on the wireless external control device 894 may be utilized in real-time for practice printing virtual objects utilizing an augmented reality display 904, a virtual reality display 906, and/or a mixed reality display (not shown). The operator may move the wireless external control device 894 and the comparable movements and dispensing actions may be enacted virtually through a computer program using augmented reality, virtual reality, and/or mixed reality. This will allow the operator to practice multiple printing of virtual objects prior to printing an actual object without wasting valuable structural material and/or valuable biological materials. The files for printing in an augmented reality, virtual reality, and/or mixed reality environment may be saved in a memory storage device and executed using the automated control assembly 880 and/or the large-scale single-use biological 3D printer 910.

The purpose of the robotic arm assembly 854 is to move, manipulate, and dispense materials from the dispensing device 856 internal to the sterilized chamber 852 while the operator is operating comfortably outside of the sterilized chamber 852. Indeed, operating within an isolator or glovebox typically means dealing with bulky gloves, so that the fine controls of dispensing materials into a small printing tray or multi-well plate 858 may not be adequately maneuvered.

The transfer hatch 860 may be utilized to remove objects aseptically from the sterilized chamber 852 and/or to connect to additional sterilized chambers to form a more complex assembly. The robotic arm assemblies may additionally be utilized to move materials from one sterilized chamber to another through the connected transfer hatches 860.

The large-scale single-use biological 3D printer 910 may be operated within a sterile chamber 912 with a printing platform 918 driven by a hydraulically and/or pneumatically linear actuator and a printer head 926 featuring a plurality of articulating axis joints 922 and 924 as described in U.S. patent application Ser. No. 14/927,848, which is incorporated herein by reference. The at least two articulating axis joints 922 and 924 on the printer head 926 allow for the positioning of a printer head dispenser 928 at a plurality of angles in relation to the printing tray 920. The hydraulically- and/or pneumatically-driven linear actuators 914 and 916 are extended at different heights resulting in the printing platform 918 and printing tray 920 to be positioned at an angle in relation to the printer head dispenser 928. The multi-axis positioning of the printing tray 920 at a plurality of angles, as well as the multi-axis positioning of the printer head dispenser 928, allows for additional degrees of freedom and increased flexibility for printing with a printer setup over a standard 3-axis coordinate printing system. These additional degrees of freedom mimic the movements an operator would make during the printing of an object with the dispensing device 856 device and/or the wireless external control device 894.

What is claimed is:

1. A dispensing system comprising:
   a sterilizable chamber;
   a dispensing device within the sterilizable chamber, the dispensing device having a dispensing end and comprising:
   a first dispensing element having a first dispensing tip at the dispensing end of the dispensing device, at least one motor and at least one gear for feeding a first material toward a first dispensing tip, the first dispensing tip being configured for dispensing a first material from the first dispensing element into a first selected location in the sterilizable chamber external of the dispensing device, a second dispensing element having a second dispensing tip at the dispensing end of the dispensing device and in a position spaced from the first dispensing tip, the second dispensing tip being configured for dispensing a second material from the second dispensing element into a second selected location in the sterilizable chamber external of the dispensing device, the second material being different from the first material, at least one location on the first dispensing element spaced from the first dispensing tip being releasably connected directly to at least one location on the second dispensing element spaced from the second dispensing tip so that the first and second dispensing elements are directly physically contacting one another when the first and second dispensing elements are in a position for dispensing the first and second materials respectively, the at least one location on the first dispensing element spaced from the first dispensing tip that is releasably connected directly to at least one location on the second dispensing element spaced from the second dispensing tip is configured to achieve at least one of a power connection and a data connection between the first and second dispensing elements, and a dispense control mechanism that is selectively operable for permitting the first material to be dispensed from the first dispensing tip of the first dispensing element or permitting the second material to be dispensed from the second dispensing tip of the second dispensing element;

at least one robotic arm assembly within the sterilizable chamber and configured to move the dispensing device within the sterilizable chamber; and an external control device connected to the at least one robotic arm assembly and to the dispense control mechanism, the external control device being configured to control the at least one robotic arm assembly for moving the dispensing device and further having a material selector for controlling the dispense control mechanism on the dispensing element for dispensing one of the first and second materials;

wherein the first dispensing element is configured to dispense a structural material as the first material and the second dispensing element is configured to dispense a biological material as the second material.

2. The dispensing system of claim 1, further comprising at least one tubing line filled with a sterile fluid, the at least one tubing line configured to control the movements of the at least one robotic arm assembly by means of a pressure exercised by the sterile fluid.

3. The dispensing system of claim 1, wherein the external control device is manually operable.

4. The dispensing system of claim 1, wherein the external control device is an automated control assembly comprising a wireless communication device and the dispensing system further comprises a wireless external input controller in communication with the wireless communication device.

5. The dispensing system of claim 4, further comprising a computing device and wherein the wireless external input controller further comprises positional sensors and is configured to communicate data from the positional sensors to the computing device, wherein the computing device is configured to virtually replicate movements of the wireless external input controller.

6. The dispensing system of claim 1, wherein the at least one robotic arm assembly is connected to the second dispensing element.

7. The dispensing system of claim 1, wherein the dispensing device has a specified shape and wherein the external control device has a shape that is substantially the same as the specified shape of the dispensing device thereby enabling an operator to carry out a control device movement that simulates a desired dispensing device movement and that generates the desired dispensing device movement simulated by the control device movement carried out by the operator.

8. The dispensing system of claim 1, wherein the first and second dispensing tips are dimensioned differently.

9. The dispensing system of claim 1, wherein the dispense control mechanism includes a material selector switch that is selectively movable between a first position for permitting the first material to be dispensed from the first dispensing tip of the first dispensing element or a second position for permitting the second material to be dispensed from the second dispensing tip of the second dispensing element, wherein the material selector switch of the dispense control mechanism is moved from a first position for selecting the first dispensing element to a second position for selecting the second dispensing element.

10. The dispensing system of claim 1, wherein the second dispensing element is sterilizable.

11. The dispensing system of claim 1, further comprising:
a heating element incorporated in the first dispensing element adjacent the first dispensing tip and configured to enable regulation of a temperature of the first material dispensed from the first dispensing tip;
a thermally-shielding barrier disposed for shielding at least parts of the second dispensing element from the heating element in the first dispensing element.

* * * * *